US006455762B1

(12) United States Patent
Chiang et al.

(10) Patent No.: US 6,455,762 B1
(45) Date of Patent: Sep. 24, 2002

(54) METHODS OF MODIFYING LIGNIN IN PLANTS BY TRANSFORMATION WITH A 4-COUMARATE COENZYME A LIGASE NUCLEIC ACID

(75) Inventors: Vincent Lee C. Chiang; Chung-Jui Tsai, both of Hancock, MI (US); Wen-Jing Hu, Houston, TX (US)

(73) Assignee: Board of Control of Michigan Technological University, Houghton, MI (US)

( * ) Notice: Subject to any disclaimer, the term of this patent is extended or adjusted under 35 U.S.C. 154(b) by 0 days.

(21) Appl. No.: 08/969,046

(22) Filed: Nov. 12, 1997

(51) Int. Cl.[7] .......................... A01H 5/00; C12N 15/82
(52) U.S. Cl. ...................... 800/298; 800/278; 800/279; 800/286; 800/294; 800/301
(58) Field of Search .................... 536/23.6; 425/468, 425/295, 419, 410; 800/285, 278, 290, 279, 286, 294, 298, 301

(56) References Cited

U.S. PATENT DOCUMENTS

| 5,107,065 | A | | 4/1992 | Shewmaker et al. ........ 800/205 |
| 5,190,931 | A | | 3/1993 | Inouye ........................ 435/91 |
| 5,850,020 | A | * | 12/1998 | Bloksberg et al. .......... 800/205 |
| 5,952,486 | A | * | 9/1999 | Bloksberg et al. .......... 536/23.6 |
| 6,204,434 | B1 | * | 3/2001 | Bloksberg et al. .......... 800/290 |

FOREIGN PATENT DOCUMENTS

| WO | 93/05160 | 3/1993 | ........... C12N/15/54 |
| WO | WO 98/11205 | 3/1998 | |
| WO | 98/11205 | 3/1998 | ............ C12N/9/02 |

OTHER PUBLICATIONS

GenBank Accession No. M62755, 1993.*
GenBank Accession No. X13324, 1993.*
GenBank Accession No. U12012, 1996.*
GenBank Accession No. U12013, 1996.*
GenBank Accession No. X52623, 1993.*
Haung et al. In Vitro Cellular and Developmental Biology. 1991. vol. 27P: 201–207.*
Kajita et al. 1996. Plant Cell Physiol. vol.: 37: 957–965.*
Napoli et al. The Plant Cell. 1989. vol. 2: 278–289.*
Smith et al. Nature. 1988. vol. 334: 724–726.*
Tsai et al. Plant Cell Reports. 1994. vol. 14: 94–97.*
Lee et al. Plant Molecular Biology, 1995. vol. 28: 871–884.*
Ehlting et al, Three 4–coumarate: coenzyme A ligases in *Arabidopsis thaliana* represent two evolutionary divergent classes in angiosperms:, *The Plant Journal*, 19 (1) 9–20 (1991).
Dandekar, A.M., et al., "Transformation and Foreign Gene Expression in Micropropageted Douglas–Fir (*Pseudotsuga menziesii*)", *Bio/technolgy*, 5, 587–590 (Jun. 1987).
Douglas, C.J., et al., "Exonic Sequences Are Required for Elicitor and Light Activation of a Plant Defense Gene, but Promoter Sequences Are Sufficient for Tissue Specific Expression", *The EMBO Journal*, 10, 1767–1775 (1991).

Fillatti, J.J., et al., "Agrobacterium Mediated Transformation and Regeneration of Populus", *Molecular and General Genetics*, 206, 192–199 (1987).
Hu, W., et al., "Compartmentized Expression of Two Structurally and Functionally Distinct 4–Coumarate:CoA Ligase Genes in Aspen (*Populus tremuloides*)", *Proc. Natl. Acad. Sci. USA*, 95, 5407–5412 (Apr. 1998).
Huang, Y., et al., "*Agrobacterium rhizogenes*–Mediated Genetic Transformation and Regeneration of a Conifer: *Larix decidua*", In Vitro *Cell. Dev. Biol.*, 27P, 201–207 (Oct. 1991).
Kajita, S., et al., "Alterations in the Biosynthesis of Lignin in Transgenic Plants with Chimeric Genes for 4–Coumarate:Coenzyme A Ligase", *Plant Cell Physiology*, 37, 957–965, (1996).
McGranahan, G.H., et al., "Agrobacterium–Mediated Transformation of Walnut Somatic Embryos and Regeneration of Transgenic Plants", *Bio/technology*, 6, 800–804, (Jul. 1988).
Minocha, S.C., et al., "Tissue Culture and Genetic Transformation in *Betula Papyrifera* and *Populus Tremuloides*", Proceedings, 1986 TAPPI Research and Development Conference, Raleigh, NC, 89–92 (Sep. 28–Oct. 1, 1986).
Sullivan, J., et al., "Transformation of *Liquiambar styraciflua* using *Agrobacterium tumefaciens*", *Plant Cell Reports*, 12, 303–306 (1993).
Uhlmann, A., et al., "Molecular Cloning and Expression of 4–Coumarate:coenzyme A Ligase, an Enzyme Involved in the Resistance Response of Soybean (*Glycine Max* L.) Against Pathogen Attack", *Plant Physiology*, 102, 1147–1156 (1993).
Wilde, H.D., et al., "Expression of Foreign Genes in Transgenic Yellow–Poplar Plants", *Plant Physiology*, 98, 114–120 (1992).
Zhang, X., et al., "Molecular Cloning of 4–Coumarate:Coenzyme A Ligase in Loblolly Pine and the Roles of the Enzyme in the Biosynthesis of Lignin in Compression Wood", *Plant Physiology*, 113, 65–74 (1997).
Kajita, et al. "Alterations in the Biosynthesis of Lignin in Transgenic Plants with Chimeric Genes for 4–Coumarate:Coenzyme A Ligase", Plant Cell Physiol., 37(7): pp. 957–965, 1966.
Holmberg, et al. "Transgenic Tobacco Expressing Vitreoscilla Hemoglobin Exhibits Enhanced Growth and Altered Metabolite Production", *Nature Biotechnology*, vol. 15, pp. 244–247, Mar. 1997.
Doerner, et al. "Control of Root Growth and Development by Cyclin Expression", *Nature*, vol. 380, pp. 520–523, Apr. 11, 1996.
Szerszen, et al. "iaglu, a Gene from *Zea mays* Involved in Conjugation of Growth Hormone Indole–3–Acetic Acid", *Science*, vol. 265, pp. 1699–1701, Sep. 16, 1994.

* cited by examiner

*Primary Examiner*—Amy J. Nelson
(74) *Attorney, Agent, or Firm*—Joseph A. Gemignani; Teresa J. Welch; Sara Dastgheib-Vinarov

(57) ABSTRACT

The invention pertains to methods of altering growth, lignin content, coniferyl and sinapyl alcohol units in the lignin structure, disease resistance and cellulose content in plants by transformation with a lignin pathway p-coumarate Co-enzyme A ligase (4CL) nucleic acid.

38 Claims, 8 Drawing Sheets

SEQUENCE LISTING

<160> NUMBER OF SEQ ID NOS: 15

<210> SEQ ID NO 1
<211> LENGTH: 1915
<212> TYPE: DNA
<213> ORGANISM: Populus tremuloides Michx.
<220> FEATURE:
<221> NAME/KEY: CDS
<222> LOCATION: (83)...(1687)

<400> SEQUENCE: 1

```
ccctcgcgaa actccgaaaa cagagagcac ctaaaactca ccatctctcc ctctgcatct         60
ttagcccgca atggacgcca ca atg aat cca caa gaa ttc atc ttt cgc tca        112
                         Met Asn Pro Gln Glu Phe Ile Phe Arg Ser
                         1               5                  10
```

-continued

| | | |
|---|---|---|
| aaa tta cca gac atc tac atc ccg aaa aac ctt ccc ctg cat tca tac<br>Lys Leu Pro Asp Ile Tyr Ile Pro Lys Asn Leu Pro Leu His Ser Tyr<br>                       15                            20                      25 | 160 |

```
aaa tta cca gac atc tac atc ccg aaa aac ctt ccc ctg cat tca tac     160
Lys Leu Pro Asp Ile Tyr Ile Pro Lys Asn Leu Pro Leu His Ser Tyr
             15                  20                  25 gtt ctt gag aac ttg tct aaa cat tca tca aaa cct tgc cta ata aat     208
Val Leu Glu Asn Leu Ser Lys His Ser Ser Lys Pro Cys Leu Ile Asn
         30                  35                  40 ggc gcg aat gga gat gtc tac acc tat gct gat gtt gag ctc aca gca     256
Gly Ala Asn Gly Asp Val Tyr Thr Tyr Ala Asp Val Glu Leu Thr Ala
     45                  50                  55 aga aga gtt gct tct ggt ctg aac aag att ggt att caa caa ggt gac     304
Arg Arg Val Ala Ser Gly Leu Asn Lys Ile Gly Ile Gln Gln Gly Asp
 60                  65                  70 gtg atc atg ctc ttc cta cca agt tca cct gaa ttc gtg ctt gct ttc     352
Val Ile Met Leu Phe Leu Pro Ser Ser Pro Glu Phe Val Leu Ala Phe
 75                  80                  85                  90 cta ggc gct tca cac aga ggt gcc atg atc act gct gcc aat cct ttc     400
Leu Gly Ala Ser His Arg Gly Ala Met Ile Thr Ala Ala Asn Pro Phe
                 95                 100                 105 tcc acc cct gca gag cta gca aaa cat gcc aag gcc tcg aga gca aag     448
Ser Thr Pro Ala Glu Leu Ala Lys His Ala Lys Ala Ser Arg Ala Lys
             110                 115                 120 ctt ctg ata aca cag gct tgt tac tac gag aag gtt aaa gat ttt gcc     496
Leu Leu Ile Thr Gln Ala Cys Tyr Tyr Glu Lys Val Lys Asp Phe Ala
         125                 130                 135 cga gaa agt gat gtt aag gtc atg tgc gtg gac tct gcc ccg gac ggt     544
Arg Glu Ser Asp Val Lys Val Met Cys Val Asp Ser Ala Pro Asp Gly
     140                 145                 150 gct tca ctt ttc aga gct cac aca cag gca gac gaa aat gaa gtg cct     592
Ala Ser Leu Phe Arg Ala His Thr Gln Ala Asp Glu Asn Glu Val Pro
155                 160                 165                 170 cag gtc gac att agt cct gat gat gtc gta gca ttg cct tat tca tca     640
Gln Val Asp Ile Ser Pro Asp Asp Val Val Ala Leu Pro Tyr Ser Ser
                 175                 180                 185 ggg act aca ggg ttg cca aaa ggg gtc atg tta acg cac aaa ggg cta     688
Gly Thr Thr Gly Leu Pro Lys Gly Val Met Leu Thr His Lys Gly Leu
             190                 195                 200 ata acc agt gtg gct caa cag gta gat gga gac aat cct aac ctg tat     736
Ile Thr Ser Val Ala Gln Gln Val Asp Gly Asp Asn Pro Asn Leu Tyr
         205                 210                 215 ttt cac agt gaa gat gtg att ctg tgt gtg ctt cct atg ttc cat atc     784
Phe His Ser Glu Asp Val Ile Leu Cys Val Leu Pro Met Phe His Ile
     220                 225                 230 tat gct ctg aat tca atg atg ctc tgt ggt ctg aga gtt ggt gcc tcg     832
Tyr Ala Leu Asn Ser Met Met Leu Cys Gly Leu Arg Val Gly Ala Ser
235                 240                 245                 250 att ttg ata atg cca aag ttt gag att ggt tct ttg ctg gga ttg att     880
Ile Leu Ile Met Pro Lys Phe Glu Ile Gly Ser Leu Leu Gly Leu Ile
                 255                 260                 265 gag aag tac aag gta tct ata gca cca gtt gtt cca cct gtg atg atg     928
Glu Lys Tyr Lys Val Ser Ile Ala Pro Val Val Pro Pro Val Met Met
             270                 275                 280 gca att gct aag tca cct gat ctt gac aag cat gac ctg tct tct ttg     976
Ala Ile Ala Lys Ser Pro Asp Leu Asp Lys His Asp Leu Ser Ser Leu
         285                 290                 295 agg atg ata aaa tct gga ggg gct cca ttg ggc aag gaa ctt gaa gat    1024
Arg Met Ile Lys Ser Gly Gly Ala Pro Leu Gly Lys Glu Leu Glu Asp
     300                 305                 310 act gtc aga gct aag ttt cct cag gct aga ctt ggt cag gga tat gga    1072
Thr Val Arg Ala Lys Phe Pro Gln Ala Arg Leu Gly Gln Gly Tyr Gly
315                 320                 325                 330
```

-continued

```
atg acc gag gca gga cct gtt cta gca atg tgc ttg gca ttt gcc aag      1120
Met Thr Glu Ala Gly Pro Val Leu Ala Met Cys Leu Ala Phe Ala Lys
            335                 340                 345 gaa cca ttc gac ata aaa cca ggt gca tgt gga act gta gtc agg aat      1168
Glu Pro Phe Asp Ile Lys Pro Gly Ala Cys Gly Thr Val Val Arg Asn
        350                 355                 360 gca gag atg aag att gtt gac cca gaa aca ggg gtc tct cta ccg agg      1216
Ala Glu Met Lys Ile Val Asp Pro Glu Thr Gly Val Ser Leu Pro Arg
    365                 370                 375 aac cag cct ggt gag atc tgc atc cgg ggt gat cag atc atg aaa gga      1264
Asn Gln Pro Gly Glu Ile Cys Ile Arg Gly Asp Gln Ile Met Lys Gly
380                 385                 390 tat ctt aat gac ccc gag gca acc tca aga aca ata gac aaa gaa gga      1312
Tyr Leu Asn Asp Pro Glu Ala Thr Ser Arg Thr Ile Asp Lys Glu Gly
395                 400                 405                 410 tgg ctg cac aca ggc gat atc ggc tac att gat gat gat gat gag ctt      1360
Trp Leu His Thr Gly Asp Ile Gly Tyr Ile Asp Asp Asp Asp Glu Leu
                415                 420                 425 ttc atc gtt gac aga ttg aag gaa ttg atc aag tat aaa ggg ttt cag      1408
Phe Ile Val Asp Arg Leu Lys Glu Leu Ile Lys Tyr Lys Gly Phe Gln
            430                 435                 440 gtt gct cct act gaa ctc gaa gct ttg tta ata gcc cat cca gag ata      1456
Val Ala Pro Thr Glu Leu Glu Ala Leu Leu Ile Ala His Pro Glu Ile
        445                 450                 455 tcc gat gct gct gta gta gga ttg aaa gat gag gat gcg gga gaa gtt      1504
Ser Asp Ala Ala Val Val Gly Leu Lys Asp Glu Asp Ala Gly Glu Val
    460                 465                 470 cct gtt gca ttt gta gtg aaa tca gaa aag tct cag gcc acc gaa gat      1552
Pro Val Ala Phe Val Val Lys Ser Glu Lys Ser Gln Ala Thr Glu Asp
475                 480                 485                 490 gaa att aag cag tat att tca aaa cag gtg atc ttc tac aag aga ata      1600
Glu Ile Lys Gln Tyr Ile Ser Lys Gln Val Ile Phe Tyr Lys Arg Ile
                495                 500                 505 aaa cga gtt ttc ttc att gaa gca att ccc aag gca cca tca ggc aag      1648
Lys Arg Val Phe Phe Ile Glu Ala Ile Pro Lys Ala Pro Ser Gly Lys
            510                 515                 520 atc ctg agg aag aat ctg aaa gag aag ttg cca ggc ata taactgaaga      1697
Ile Leu Arg Lys Asn Leu Lys Glu Lys Leu Pro Gly Ile
        525                 530             535 tgttactgaa catttaaccc tctgtcttat ttctttaata cttgcgaatc attgtagtgt   1757
tgaaccaagc atgcttggaa aagacacgta cccaacgtaa gacagttact gttcctagta   1817
tacaagctct ttaatgttcg ttttgaactt gggaaaacat aagttctcct gtcgccatat   1877
ggagtaattc aattgaatat tttggtttct ttaatgat                           1915

<210> SEQ ID NO 2
<211> LENGTH: 535
<212> TYPE: PRT
<213> ORGANISM: Populus tremuloides Michx.

<400> SEQUENCE: 2

Met Asn Pro Gln Glu Phe Ile Phe Arg Ser Lys Leu Pro Asp Ile Tyr
 1               5                  10                  15

Ile Pro Lys Asn Leu Pro Leu His Ser Tyr Val Leu Glu Asn Leu Ser
            20                  25                  30

Lys His Ser Ser Lys Pro Cys Leu Ile Asn Gly Ala Asn Gly Asp Val
        35                  40                  45

Tyr Thr Tyr Ala Asp Val Glu Leu Thr Ala Arg Arg Val Ala Ser Gly
```

-continued

```
            50                  55                  60
Leu Asn Lys Ile Gly Ile Gln Gln Gly Asp Val Ile Met Leu Phe Leu
 65                  70                  75                  80

Pro Ser Ser Pro Glu Phe Val Leu Ala Phe Leu Gly Ala Ser His Arg
                 85                  90                  95

Gly Ala Met Ile Thr Ala Ala Asn Pro Phe Ser Thr Pro Ala Glu Leu
            100                 105                 110

Ala Lys His Ala Lys Ala Ser Arg Ala Lys Leu Leu Ile Thr Gln Ala
        115                 120                 125

Cys Tyr Tyr Glu Lys Val Lys Asp Phe Ala Arg Glu Ser Asp Val Lys
        130                 135                 140

Val Met Cys Val Asp Ser Ala Pro Asp Gly Ala Ser Leu Phe Arg Ala
145                 150                 155                 160

His Thr Gln Ala Asp Glu Asn Glu Val Pro Gln Val Asp Ile Ser Pro
                165                 170                 175

Asp Asp Val Val Ala Leu Pro Tyr Ser Ser Gly Thr Thr Gly Leu Pro
                180                 185                 190

Lys Gly Val Met Leu Thr His Lys Gly Leu Ile Thr Ser Val Ala Gln
            195                 200                 205

Gln Val Asp Gly Asp Asn Pro Asn Leu Tyr Phe His Ser Glu Asp Val
        210                 215                 220

Ile Leu Cys Val Leu Pro Met Phe His Ile Tyr Ala Leu Asn Ser Met
225                 230                 235                 240

Met Leu Cys Gly Leu Arg Val Gly Ala Ser Ile Leu Ile Met Pro Lys
                245                 250                 255

Phe Glu Ile Gly Ser Leu Leu Gly Leu Ile Glu Lys Tyr Lys Val Ser
            260                 265                 270

Ile Ala Pro Val Val Pro Pro Val Met Met Ala Ile Ala Lys Ser Pro
        275                 280                 285

Asp Leu Asp Lys His Asp Leu Ser Ser Leu Arg Met Ile Lys Ser Gly
        290                 295                 300

Gly Ala Pro Leu Gly Lys Glu Leu Glu Asp Thr Val Arg Ala Lys Phe
305                 310                 315                 320

Pro Gln Ala Arg Leu Gly Gln Gly Tyr Gly Met Thr Glu Ala Gly Pro
                325                 330                 335

Val Leu Ala Met Cys Leu Ala Phe Ala Lys Glu Pro Phe Asp Ile Lys
            340                 345                 350

Pro Gly Ala Cys Gly Thr Val Val Arg Asn Ala Glu Met Lys Ile Val
        355                 360                 365

Asp Pro Glu Thr Gly Val Ser Leu Pro Arg Asn Gln Pro Gly Glu Ile
        370                 375                 380

Cys Ile Arg Gly Asp Gln Ile Met Lys Gly Tyr Leu Asn Asp Pro Glu
385                 390                 395                 400

Ala Thr Ser Arg Thr Ile Asp Lys Glu Gly Trp Leu His Thr Gly Asp
                405                 410                 415

Ile Gly Tyr Ile Asp Asp Asp Glu Leu Phe Ile Val Asp Arg Leu
            420                 425                 430

Lys Glu Leu Ile Lys Tyr Lys Gly Phe Gln Val Ala Pro Thr Glu Leu
        435                 440                 445

Glu Ala Leu Leu Ile Ala His Pro Glu Ile Ser Asp Ala Ala Val Val
        450                 455                 460

Gly Leu Lys Asp Glu Asp Ala Gly Glu Val Pro Val Ala Phe Val Val
465                 470                 475                 480
```

```
Lys Ser Glu Lys Ser Gln Ala Thr Glu Asp Glu Ile Lys Gln Tyr Ile
            485                 490                 495

Ser Lys Gln Val Ile Phe Tyr Lys Arg Ile Lys Arg Val Phe Phe Ile
            500                 505                 510

Glu Ala Ile Pro Lys Ala Pro Ser Gly Lys Ile Leu Arg Lys Asn Leu
            515                 520                 525

Lys Glu Lys Leu Pro Gly Ile
            530             535

<210> SEQ ID NO 3
<211> LENGTH: 1710
<212> TYPE: DNA
<213> ORGANISM: Populus tremuloides Michx.
<220> FEATURE:
<221> NAME/KEY: CDS
<222> LOCATION: (1)...(1710)

<400> SEQUENCE: 3 atg atg tcc gtg gcc acg gtt gag ccc ccg aaa ccg gaa ctc tcc cct      48
Met Met Ser Val Ala Thr Val Glu Pro Pro Lys Pro Glu Leu Ser Pro
  1               5                  10                  15 cca caa aac caa aac gca cca tcc tct cat gaa act gat cac att ttc     96
Pro Gln Asn Gln Asn Ala Pro Ser Ser His Glu Thr Asp His Ile Phe
             20                  25                  30 aga tca aaa cta cca gac ata acc atc tcg aac gac ctc cct ctg cac    144
Arg Ser Lys Leu Pro Asp Ile Thr Ile Ser Asn Asp Leu Pro Leu His
         35                  40                  45 gca tac tgc ttt gaa aac ctc tct gat ttc tca gat agg cca tgc ttg    192
Ala Tyr Cys Phe Glu Asn Leu Ser Asp Phe Ser Asp Arg Pro Cys Leu
     50                  55                  60 att tca ggt tcc acg gga aaa acc tat tct ttt gcc gaa act cac ctc    240
Ile Ser Gly Ser Thr Gly Lys Thr Tyr Ser Phe Ala Glu Thr His Leu
 65                  70                  75                  80 ata tct cgg aag gtc gct gct ggg tta tcc aat ttg ggc atc aag aaa    288
Ile Ser Arg Lys Val Ala Ala Gly Leu Ser Asn Leu Gly Ile Lys Lys
                 85                  90                  95 ggc gat gta atc atg acc ctg ctc caa aac tgc cca gaa ttc gtc ttc    336
Gly Asp Val Ile Met Thr Leu Leu Gln Asn Cys Pro Glu Phe Val Phe
            100                 105                 110 tcc ttc atc ggt gct tcc atg att ggt gca gtc atc acc act gcg aac    384
Ser Phe Ile Gly Ala Ser Met Ile Gly Ala Val Ile Thr Thr Ala Asn
        115                 120                 125 cct ttc tac act caa agt gaa ata ttc aag caa ttc tct gct tct cgt    432
Pro Phe Tyr Thr Gln Ser Glu Ile Phe Lys Gln Phe Ser Ala Ser Arg
    130                 135                 140 gcg aaa ctg att atc acc cag tct caa tat gtg aac aag cta gga gat    480
Ala Lys Leu Ile Ile Thr Gln Ser Gln Tyr Val Asn Lys Leu Gly Asp
145                 150                 155                 160 agt gat tgc cat gaa aac aac caa aaa ccg ggg gaa gat ttc ata gta    528
Ser Asp Cys His Glu Asn Asn Gln Lys Pro Gly Glu Asp Phe Ile Val
                165                 170                 175 atc acc att gat gac ccg cca gag aac tgt cta cat ttc aat gtg ctt    576
Ile Thr Ile Asp Asp Pro Pro Glu Asn Cys Leu His Phe Asn Val Leu
            180                 185                 190 gtc gag gct agc gag agt gaa atg cca aca gtt tca atc ctt ccg gat    624
Val Glu Ala Ser Glu Ser Glu Met Pro Thr Val Ser Ile Leu Pro Asp
        195                 200                 205 gat cct gtg gca tta cca ttc tct tca ggg aca aca ggg ctc cca aaa    672
Asp Pro Val Ala Leu Pro Phe Ser Ser Gly Thr Thr Gly Leu Pro Lys
    210                 215                 220
```

```
gga gtg ata ctg acc cac aag agc ttg ata aca agt gtg gct caa caa      720
Gly Val Ile Leu Thr His Lys Ser Leu Ile Thr Ser Val Ala Gln Gln
225                 230                 235                 240 gtt gat gga gag atc cca aat tta tac ttg aaa caa gat gac gtt gtt      768
Val Asp Gly Glu Ile Pro Asn Leu Tyr Leu Lys Gln Asp Asp Val Val
                245                 250                 255 tta tgc gtt tta cct ttg ttt cac atc ttt tca ttg aac agc gtg ttg      816
Leu Cys Val Leu Pro Leu Phe His Ile Phe Ser Leu Asn Ser Val Leu
            260                 265                 270 tta tgc tcg ttg aga gcc ggt tct gct gtt ctt tta atg caa aag ttt      864
Leu Cys Ser Leu Arg Ala Gly Ser Ala Val Leu Leu Met Gln Lys Phe
        275                 280                 285 gag ata gga tca ctg cta gag ctc att cag aaa cac aat gtt tcg gtt      912
Glu Ile Gly Ser Leu Leu Glu Leu Ile Gln Lys His Asn Val Ser Val
    290                 295                 300 gcg gct gtg gtt cca cca ctg gtg ctg gcg ttg gcc aag aac cca ttg      960
Ala Ala Val Val Pro Pro Leu Val Leu Ala Leu Ala Lys Asn Pro Leu
305                 310                 315                 320 gag gcg aac ttc gac ttg agt tcg atc agg gta gtc ctg tca ggg gct     1008
Glu Ala Asn Phe Asp Leu Ser Ser Ile Arg Val Val Leu Ser Gly Ala
                325                 330                 335 gcg cca ctg ggg aag gag ctc gag gac gcc ctc agg agc agg gtt cct     1056
Ala Pro Leu Gly Lys Glu Leu Glu Asp Ala Leu Arg Ser Arg Val Pro
            340                 345                 350 cag gcc atc ctg gga cag ggt tat ggg atg aca gag gcc ggg cct gtg     1104
Gln Ala Ile Leu Gly Gln Gly Tyr Gly Met Thr Glu Ala Gly Pro Val
        355                 360                 365 cta tca atg tgc tta gcc ttt tca aag caa cct ttc cca acc aag tct     1152
Leu Ser Met Cys Leu Ala Phe Ser Lys Gln Pro Phe Pro Thr Lys Ser
    370                 375                 380 ggg tcg tgt gga acg gtg gtt aga aac gca gag ctc aag gtc att gac     1200
Gly Ser Cys Gly Thr Val Val Arg Asn Ala Glu Leu Lys Val Ile Asp
385                 390                 395                 400 cct gag acc ggt cgc tct ctt ggt tac aac caa cct ggt gaa atc tgc     1248
Pro Glu Thr Gly Arg Ser Leu Gly Tyr Asn Gln Pro Gly Glu Ile Cys
                405                 410                 415 atc cgt gga tcc caa atc atg aaa gga tat ttg aat gac gcg gaa gcc     1296
Ile Arg Gly Ser Gln Ile Met Lys Gly Tyr Leu Asn Asp Ala Glu Ala
            420                 425                 430 acg gca aac acc ata gac gtt gag ggt tgg ctc cac act gga gat ata     1344
Thr Ala Asn Thr Ile Asp Val Glu Gly Trp Leu His Thr Gly Asp Ile
        435                 440                 445 ggt tat gtc gac gac gac gac gag att ttc att gtt gat aga gtg aag     1392
Gly Tyr Val Asp Asp Asp Asp Glu Ile Phe Ile Val Asp Arg Val Lys
    450                 455                 460 gaa atc ata aaa ttc aaa ggc ttc cag gtg ccg cca gcg gag ctt gag     1440
Glu Ile Ile Lys Phe Lys Gly Phe Gln Val Pro Pro Ala Glu Leu Glu
465                 470                 475                 480 gct ctc ctt gta aac cac cct tca att gcg gat gcg gct gtt gtt ccg     1488
Ala Leu Leu Val Asn His Pro Ser Ile Ala Asp Ala Ala Val Val Pro
                485                 490                 495 caa aaa gac gag gtt gct ggt gaa gtt cct gtc gcg ttt gtg gtc cgc     1536
Gln Lys Asp Glu Val Ala Gly Glu Val Pro Val Ala Phe Val Val Arg
            500                 505                 510 tca gat gat ctt gac ctt agt gaa gag gct gta aaa gaa tac att gca     1584
Ser Asp Asp Leu Asp Leu Ser Glu Glu Ala Val Lys Glu Tyr Ile Ala
        515                 520                 525 aag cag gtg gtg ttc tac aag aaa ctg cac aag gtg ttc ttc gtt cat     1632
Lys Gln Val Val Phe Tyr Lys Lys Leu His Lys Val Phe Phe Val His
```

```
                530              535             540
tct att ccc aaa tcg gct tct gga aag att cta aga aaa gac ctc aga    1680
Ser Ile Pro Lys Ser Ala Ser Gly Lys Ile Leu Arg Lys Asp Leu Arg
545                 550             555                 560 gcc aag ctt gcc aca gcc acc acc atg tcc                            1710
Ala Lys Leu Ala Thr Ala Thr Thr Met Ser
                565             570
```

<210> SEQ ID NO 4
<211> LENGTH: 570
<212> TYPE: PRT
<213> ORGANISM: Populus tremuloides Michx.

<400> SEQUENCE: 4

```
Met Met Ser Val Ala Thr Val Glu Pro Pro Lys Pro Glu Leu Ser Pro
1               5                   10                  15

Pro Gln Asn Gln Asn Ala Pro Ser Ser His Glu Thr Asp His Ile Phe
                20                  25                  30

Arg Ser Lys Leu Pro Asp Ile Thr Ile Ser Asn Asp Leu Pro Leu His
            35                  40                  45

Ala Tyr Cys Phe Glu Asn Leu Ser Asp Phe Ser Asp Arg Pro Cys Leu
        50                  55                  60

Ile Ser Gly Ser Thr Gly Lys Thr Tyr Ser Phe Ala Glu Thr His Leu
65                  70                  75                  80

Ile Ser Arg Lys Val Ala Ala Gly Leu Ser Asn Leu Gly Ile Lys Lys
                85                  90                  95

Gly Asp Val Ile Met Thr Leu Leu Gln Asn Cys Pro Glu Phe Val Phe
                100                 105                 110

Ser Phe Ile Gly Ala Ser Met Ile Gly Ala Val Ile Thr Thr Ala Asn
            115                 120                 125

Pro Phe Tyr Thr Gln Ser Glu Ile Phe Lys Gln Phe Ser Ala Ser Arg
        130                 135                 140

Ala Lys Leu Ile Ile Thr Gln Ser Gln Tyr Val Asn Lys Leu Gly Asp
145                 150                 155                 160

Ser Asp Cys His Glu Asn Asn Gln Lys Pro Gly Glu Asp Phe Ile Val
                165                 170                 175

Ile Thr Ile Asp Asp Pro Pro Glu Asn Cys Leu His Phe Asn Val Leu
            180                 185                 190

Val Glu Ala Ser Glu Ser Glu Met Pro Thr Val Ser Ile Leu Pro Asp
        195                 200                 205

Asp Pro Val Ala Leu Pro Phe Ser Ser Gly Thr Thr Gly Leu Pro Lys
        210                 215                 220

Gly Val Ile Leu Thr His Lys Ser Leu Ile Thr Ser Val Ala Gln Gln
225                 230                 235                 240

Val Asp Gly Glu Ile Pro Asn Leu Tyr Leu Lys Gln Asp Asp Val Val
                245                 250                 255

Leu Cys Val Leu Pro Leu Phe His Ile Phe Ser Leu Asn Ser Val Leu
            260                 265                 270

Leu Cys Ser Leu Arg Ala Gly Ser Ala Val Leu Leu Met Gln Lys Phe
        275                 280                 285

Glu Ile Gly Ser Leu Leu Glu Leu Ile Gln Lys His Asn Val Ser Val
        290                 295                 300

Ala Ala Val Val Pro Pro Leu Val Leu Ala Leu Ala Lys Asn Pro Leu
305                 310                 315                 320

Glu Ala Asn Phe Asp Leu Ser Ser Ile Arg Val Val Leu Ser Gly Ala
```

```
                325                 330                 335
Ala Pro Leu Gly Lys Glu Leu Glu Asp Ala Leu Arg Ser Arg Val Pro
            340                 345                 350
Gln Ala Ile Leu Gly Gln Gly Tyr Gly Met Thr Glu Ala Gly Pro Val
            355                 360                 365
Leu Ser Met Cys Leu Ala Phe Ser Lys Gln Pro Phe Pro Thr Lys Ser
370                 375                 380
Gly Ser Cys Gly Thr Val Val Arg Asn Ala Glu Leu Lys Val Ile Asp
385                 390                 395                 400
Pro Glu Thr Gly Arg Ser Leu Gly Tyr Asn Gln Pro Gly Glu Ile Cys
            405                 410                 415
Ile Arg Gly Ser Gln Ile Met Lys Gly Tyr Leu Asn Asp Ala Glu Ala
            420                 425                 430
Thr Ala Asn Thr Ile Asp Val Glu Gly Trp Leu His Thr Gly Asp Ile
            435                 440                 445
Gly Tyr Val Asp Asp Asp Glu Ile Phe Ile Val Asp Arg Val Lys
450                 455                 460
Glu Ile Ile Lys Phe Lys Gly Phe Gln Val Pro Pro Ala Glu Leu Glu
465                 470                 475                 480
Ala Leu Leu Val Asn His Pro Ser Ile Ala Asp Ala Val Val Pro
            485                 490                 495
Gln Lys Asp Glu Val Ala Gly Glu Val Pro Val Ala Phe Val Val Arg
            500                 505                 510
Ser Asp Asp Leu Asp Leu Ser Glu Glu Ala Val Lys Glu Tyr Ile Ala
            515                 520                 525
Lys Gln Val Val Phe Tyr Lys Lys Leu His Lys Val Phe Phe Val His
            530                 535                 540
Ser Ile Pro Lys Ser Ala Ser Gly Lys Ile Leu Arg Lys Asp Leu Arg
545                 550                 555                 560
Ala Lys Leu Ala Thr Ala Thr Thr Met Ser
            565                 570

<210> SEQ ID NO 5
<211> LENGTH: 1172
<212> TYPE: DNA
<213> ORGANISM: Populus tremuloides Michx.

<400> SEQUENCE: 5
tgtaggattg gtggaatggg atcattccta atcccttaat gacggtggca tgaacacaaa     60
gcaaagagaa gttaggtcac tcctcctta tatatatata tatatgcatg catgaggacc    120
atggctatga tgaaggttaa tagaggtagt tgtgattgag atatgtccag cactagtttt    180
ttgttggtgt gatttctcat gatgacgcga aaattttata tatatata atgaataata    240 tgattgatta ttctctgtaa ttttgtgaaa tagattaaaa cagctcaatg tgaggtgacc    300
agttgtcaaa tgaccactcg acttggggca tggtgatttt tcaaatcaca actcaatttg    360
aaaactaaaa ttaaaaaga tttagattat taaattatta ggttaattca cgggttggct    420
aatcaattat tattaattaa acgatagta tttttgataa tttaattaaa attttattgg    480
atttgaatga actcaattac atcacaaaaa acctaatcaa attaatatct tatgtgatat    540
aatttagaaa tataaatgat taaccttaa atctcgagtt tctcttataa aaaacacgta    600
taattgggct agatttaaca gctattattc aaactggcca ggacaattat taaaattaat    660
aattattatt ttttctaata aagcacttcc taattgttaa aatatatgtc taaacactaa    720
```

-continued

```
taataaaatt tatttgtgta tctttggcag taggtgagag gtgctgacaa ataaattagt      780
gcataaaata taatggattg gtggtctgtg aaaagacagg tggaggacaa gccacctctc      840
tcaagtcaaa aggccatttc acaaccaacc caaatgggaa cccaccaccg ttccccgcca      900
ttaaaatccc taatctcacc aacccaactc cacagattct tcaccaaacg caactgattt      960
ttcaatcaat gttttcccta tactacccccc ccaacaactc cataataccc aatttgtcct     1020
ttcaccaacc cccgtcctcc gtgccagcca attctatatc agcaggaatg ctctgcactc     1080
tgctttctca ggtctcctac cataagaaaa cagagagcac ctaaaactcg ccatctctcc     1140
ctctgcatct ttagcccgca atggacgcga ca                                   1172
```

<210> SEQ ID NO 6
<211> LENGTH: 1180
<212> TYPE: DNA
<213> ORGANISM: Populus tremuloides Michx.

<400> SEQUENCE: 6

```
aagctttgag tattcatatg ggtattcatc cgaccattat ttttcaattt gtgttgtgtt       60
gatccaattt tcaacttatt ttttttttcac ttatttttta ttagttattt ttatttttat    120 tatttttta aaaatttaaa aattaaatta taacattttt attttatccc tcattaacta     180
aaatagggat ggtaatagat attcatgaag ggagttatat atcaaatgat attagttaag     240
ctattttgat atttataccc tactcattac ttatggaata aaaaatttag atatttataa     300
aatatttatc ggatttcagg tattcatatg aatatttatt tgattattat ttattcaaca     360
aaaaataaaa caattaatat gcatgtttga agtttatata tatattaagt taggtttaga     420
tagattttgg gtggggttaa ttaatattca taccctatct actatctatc aaataatcca     480
aataaattca cctaaattag gttgggtttg tattcatcaa gttaacatta aattgtaatt     540
ccgtaagtaa ctaaacaagt acaaagactt ctattttatc ttatatatta ccataaagcc      600
aactatattt cctattcttt ttcatcccttt ctatcgtaat tttctgtgac ttttttattt     660
atatattaac ggtaacgaaa cacagcaata aaagttattg tgaaagatat ggataattat     720
tatggtgact atgaaagagt aaatttgcca tgcactaagt tcctagtgtc atctcataaa     780
agacttgtct gccacgtaag ctgttgtgag tgtcgtttat ttacgcgtgt caaccaatcg     840
ctgccaattg actcttgagg gtaggtgaga gcttcggctt tgatgggaac tgcatgaggc     900
atagggtttg gtttcttgaa tgtgagatgg gcatgctttg gctcccttgc tactcacctc     960
atcttcaatt tgccagctca gctaccagtc tctcaccact agtttcacca aactttctct    1020
gctcctgtat ttattacacc ttgctcgatt ggctccgtcc tcgtacacgc atccacaccg    1080
atcgatcgat tagaaccata cagaattggg attggttggg tttacattct gcgttagata    1140
catctatcac agaaagaaac tcccttccat ctcaggaaac                           1180
```

<210> SEQ ID NO 7
<211> LENGTH: 11
<212> TYPE: PRT
<213> ORGANISM: Artificial Sequence
<220> FEATURE:
<223> OTHER INFORMATION: Highly conserved region of amino acids as
      determined following alignment of cloned plant CCL
      sequences.

<400> SEQUENCE: 7

Ser Ser Gly Thr Thr Gly Leu Pro Lys Gly Val
 1               5                  10

```
<210> SEQ ID NO 8
<211> LENGTH: 7
<212> TYPE: PRT
<213> ORGANISM: Artificial Sequence
<220> FEATURE:
<223> OTHER INFORMATION: Highly conserved region of amino acids as
      determined following alignment of cloned plant CCL
      sequences.

<400> SEQUENCE: 8

Gly Glu Ile Cys Ile Arg Gly
 1               5

<210> SEQ ID NO 9
<211> LENGTH: 31
<212> TYPE: DNA
<213> ORGANISM: Artificial Sequence
<220> FEATURE:
<223> OTHER INFORMATION: Sense primer designed around the first
      consensus AMP-binding region of CCL.
<220> FEATURE:
<221> NAME/KEY: modified_base
<222> LOCATION: (11)...(11)
<223> OTHER INFORMATION: I
<220> FEATURE:
<221> NAME/KEY: modified_base
<222> LOCATION: (14)...(14)
<223> OTHER INFORMATION: I
<220> FEATURE:
<221> NAME/KEY: modified_base
<222> LOCATION: (17)...(17)
<223> OTHER INFORMATION: I
<220> FEATURE:
<221> NAME/KEY: modified_base
<222> LOCATION: (20)...(20)
<223> OTHER INFORMATION: I
<220> FEATURE:
<221> NAME/KEY: modified_base
<222> LOCATION: (23)...(23)
<223> OTHER INFORMATION: I
<220> FEATURE:
<221> NAME/KEY: modified_base
<222> LOCATION: (26)...(26)
<223> OTHER INFORMATION: I

<400> SEQUENCE: 9
ttggatccgg aacaacagga ytaccaaarg g                              31

<210> SEQ ID NO 10
<211> LENGTH: 28
<212> TYPE: DNA
<213> ORGANISM: Artificial Sequence
<220> FEATURE:
<223> OTHER INFORMATION: Sense primer designed around the first
      consensus AMP-binding region of CCL.
<220> FEATURE:
<221> NAME/KEY: modified_base
<222> LOCATION: (11)...(11)
<223> OTHER INFORMATION: I
<220> FEATURE:
<221> NAME/KEY: modified_base
<222> LOCATION: (14)...(14)
<223> OTHER INFORMATION: I
<220> FEATURE:
<221> NAME/KEY: modified_base
<222> LOCATION: (23)...(23)
<223> OTHER INFORMATION: I

<400> SEQUENCE: 10
ttggatccgt agcacarcar gtagaygg                                  28

<210> SEQ ID NO 11
```

```
<211> LENGTH: 27
<212> TYPE: DNA
<213> ORGANISM: Artificial Sequence
<220> FEATURE:
<223> OTHER INFORMATION: Antisense primer designed based on the
      sequence of the putative catalytic motif GEICIRG (SEQ ID NO:12).
<220> FEATURE:
<221> NAME/KEY: modified_base
<222> LOCATION: (10)...(10)
<223> OTHER INFORMATION: I
<220> FEATURE:
<221> NAME/KEY: modified_base
<222> LOCATION: (25)...(25)
<223> OTHER INFORMATION: I

<400> SEQUENCE: 11
atgtcgacca cgdatrcada tytcacc                                           27

<210> SEQ ID NO 12
<211> LENGTH: 27
<212> TYPE: DNA
<213> ORGANISM: Artificial Sequence
<220> FEATURE:
<223> OTHER INFORMATION: Primer designed based on the genomic
      sequence of PtCCL2.

<400> SEQUENCE: 12
tctgtctaga tgatgtcgtg gccacgg                                           27

<210> SEQ ID NO 13
<211> LENGTH: 26
<212> TYPE: DNA
<213> ORGANISM: Artificial Sequence
<220> FEATURE:
<223> OTHER INFORMATION: Primer designed based on the genomic
      sequence of PtCCL2.

<400> SEQUENCE: 13
ttagatctct aggacatggt ggtggc                                            26

<210> SEQ ID NO 14
<211> LENGTH: 30
<212> TYPE: DNA
<213> ORGANISM: Artificial Sequence
<220> FEATURE:
<223> OTHER INFORMATION: A primer designed to be complementary to a
      sequence upstream of the translation start site of
      PtCCL2 and to incorporate BamH I site at the end.

<400> SEQUENCE: 14
catcggatcc tgagatggaa gggagtttct                                        30

<210> SEQ ID NO 15
<211> LENGTH: 1927
<212> TYPE: DNA
<213> ORGANISM: Petroselinum crispum
<220> FEATURE:
<221> NAME/KEY: CDS
<222> LOCATION: (64)...(1698)

<400> SEQUENCE: 15
gaattcccat catcgtttca acaccaaaaa cacacacaca actcatattt tcatattttc       60 ata atg gga gac tgt gta gca ccc aaa gaa gac ctt att ttc cga tcg        108
    Met Gly Asp Cys Val Ala Pro Lys Glu Asp Leu Ile Phe Arg Ser
    1               5                  10                  15 aaa ctc cct gat att tac atc ccg aaa cac ctt ccg tta cat act tat        156
Lys Leu Pro Asp Ile Tyr Ile Pro Lys His Leu Pro Leu His Thr Tyr
                20                  25                  30
```

-continued

| | |
|---|---|
| tgt ttc gaa aac atc tcg aaa gtt ggc gac aag tcc tgt tta ata aat<br>Cys Phe Glu Asn Ile Ser Lys Val Gly Asp Lys Ser Cys Leu Ile Asn<br>35                      40                    45 | 204 |
| ggc gct aca ggc gaa acg ttc act tat tct caa gtt gag ctc ctt tcc<br>Gly Ala Thr Gly Glu Thr Phe Thr Tyr Ser Gln Val Glu Leu Leu Ser<br>50                      55                    60 | 252 |
| agg aaa gtt gca tca ggg tta aac aaa ctc ggc att caa cag ggc gat<br>Arg Lys Val Ala Ser Gly Leu Asn Lys Leu Gly Ile Gln Gln Gly Asp<br>65                      70                    75 | 300 |
| acc atc atg ctt ttg ctc ccc aac tcc cct gag tat ttt ttc gct ttc<br>Thr Ile Met Leu Leu Leu Pro Asn Ser Pro Glu Tyr Phe Phe Ala Phe<br>80                      85                    90                    95 | 348 |
| tta ggc gca tcg tat cgt ggt gca att tct act atg gcc aat ccg ttt<br>Leu Gly Ala Ser Tyr Arg Gly Ala Ile Ser Thr Met Ala Asn Pro Phe<br>                    100                   105                 110 | 396 |
| ttc act tct gct gag gtg atc aaa cag ctc aaa gca tcc cta gct aag<br>Phe Thr Ser Ala Glu Val Ile Lys Gln Leu Lys Ala Ser Leu Ala Lys<br>                    115                   120                 125 | 444 |
| ctc ata att acg caa gct tgt tac gta gac aaa gtg aaa gac tac gca<br>Leu Ile Ile Thr Gln Ala Cys Tyr Val Asp Lys Val Lys Asp Tyr Ala<br>          130                   135                 140 | 492 |
| gca gag aaa aat ata cag atc att tgc atc gat gat gct cct cag gat<br>Ala Glu Lys Asn Ile Gln Ile Ile Cys Ile Asp Asp Ala Pro Gln Asp<br>145                     150                   155 | 540 |
| tgt tta cat ttc tcc aaa ctt atg gaa gct gat gaa tca gaa atg ccc<br>Cys Leu His Phe Ser Lys Leu Met Glu Ala Asp Glu Ser Glu Met Pro<br>160                     165                   170                 175 | 588 |
| gag gta gtg atc gat tca gac gat gtc gtc gcg tta cct tac tca tcg<br>Glu Val Val Ile Asp Ser Asp Asp Val Val Ala Leu Pro Tyr Ser Ser<br>                    180                   185                 190 | 636 |
| ggt act aca gga cta ccg aaa ggt gtt atg ttg acc cac aaa gga ctt<br>Gly Thr Thr Gly Leu Pro Lys Gly Val Met Leu Thr His Lys Gly Leu<br>                    195                   200                 205 | 684 |
| gtt act agc gtg gca caa caa gtt gat gga gac aat ccg aat tta tat<br>Val Thr Ser Val Ala Gln Gln Val Asp Gly Asp Asn Pro Asn Leu Tyr<br>210                     215                   220 | 732 |
| atg cat agc gag gat gtg atg atc tgc ata ttg cct ttg ttt cat att<br>Met His Ser Glu Asp Val Met Ile Cys Ile Leu Pro Leu Phe His Ile<br>225                     230                   235 | 780 |
| tat tcg ctt aac gcg gtg ttg tgc tgt gga ctc aga gca ggg gtg acg<br>Tyr Ser Leu Asn Ala Val Leu Cys Cys Gly Leu Arg Ala Gly Val Thr<br>240                     245                   250                 255 | 828 |
| atc ttg att atg cag aaa ttt gat att gtg cca ttt ttg gaa ctg ata<br>Ile Leu Ile Met Gln Lys Phe Asp Ile Val Pro Phe Leu Glu Leu Ile<br>                    260                   265                 270 | 876 |
| cag aaa tat aaa gtt aca att gga ccg ttt gtg cca cca att gtg ttg<br>Gln Lys Tyr Lys Val Thr Ile Gly Pro Phe Val Pro Pro Ile Val Leu<br>                    275                   280                 285 | 924 |
| gca att gcg aaa agt cca gtg gtg gat aaa tat gac ttg tcg tcg gtg<br>Ala Ile Ala Lys Ser Pro Val Val Asp Lys Tyr Asp Leu Ser Ser Val<br>                    290                   295                 300 | 972 |
| agg acg gtt atg tct gga gct gct ccg tta ggg aag gag ctt gaa gat<br>Arg Thr Val Met Ser Gly Ala Ala Pro Leu Gly Lys Glu Leu Glu Asp<br>305                     310                   315 | 1020 |
| gct gtt aga gct aag ttt cct aat gcc aaa ctt ggt cag gga tat gga<br>Ala Val Arg Ala Lys Phe Pro Asn Ala Lys Leu Gly Gln Gly Tyr Gly<br>320                     325                   330                 335 | 1068 |
| atg aca gag gca ggg cca gtt tta gca atg tgc ctg gcg ttt gca aag<br>Met Thr Glu Ala Gly Pro Val Leu Ala Met Cys Leu Ala Phe Ala Lys | 1116 |

-continued

```
                           340              345              350
gaa cca tac gag atc aaa tcg ggt gcc tgt gga act gtt gtg agg aat    1164
Glu Pro Tyr Glu Ile Lys Ser Gly Ala Cys Gly Thr Val Val Arg Asn
                355              360              365 gct gaa atg aaa att gtg gat cct gag acc aac gcc tct ctt cca cga    1212
Ala Glu Met Lys Ile Val Asp Pro Glu Thr Asn Ala Ser Leu Pro Arg
            370              375              380 aac caa cgc gga gag att tgc att cga ggt gac caa att atg aaa ggc    1260
Asn Gln Arg Gly Glu Ile Cys Ile Arg Gly Asp Gln Ile Met Lys Gly
        385              390              395 tac ctc aat gat cct gaa tca aca agg aca aca ata gac gaa gaa ggc    1308
Tyr Leu Asn Asp Pro Glu Ser Thr Arg Thr Thr Ile Asp Glu Glu Gly
400              405              410              415 tgg ttg cac aca gga gat ata ggc ttc att gac gac gat gat gag cta    1356
Trp Leu His Thr Gly Asp Ile Gly Phe Ile Asp Asp Asp Asp Glu Leu
                420              425              430 ttt att gtt gat aga ctt aag gaa ata atc aaa tac aaa ggc ttc cag    1404
Phe Ile Val Asp Arg Leu Lys Glu Ile Ile Lys Tyr Lys Gly Phe Gln
                435              440              445 gtt gcc cct gct gaa ctt gaa gct ctg cta ctt act cat cct acc att    1452
Val Ala Pro Ala Glu Leu Glu Ala Leu Leu Leu Thr His Pro Thr Ile
            450              455              460 tcc gat gct gca gtt gtt ccc atg ata gat gag aaa gca gga gag gtg    1500
Ser Asp Ala Ala Val Val Pro Met Ile Asp Glu Lys Ala Gly Glu Val
        465              470              475 cct gtg gct ttt gtt gtg aga aca aac ggt ttc acc acc act gag gaa    1548
Pro Val Ala Phe Val Val Arg Thr Asn Gly Phe Thr Thr Thr Glu Glu
480              485              490              495 gaa atc aag caa ttc gtc tcg aaa cag gtg gtg ttc tac aag aga ata    1596
Glu Ile Lys Gln Phe Val Ser Lys Gln Val Val Phe Tyr Lys Arg Ile
                500              505              510 ttt cgt gta ttt ttt gtt gat gca att ccg aaa tca cca tct gga aag    1644
Phe Arg Val Phe Phe Val Asp Ala Ile Pro Lys Ser Pro Ser Gly Lys
                515              520              525 att ctt cga aag gac ttg aga gca aaa ata gca tcc ggt gat ctt ccc    1692
Ile Leu Arg Lys Asp Leu Arg Ala Lys Ile Ala Ser Gly Asp Leu Pro
            530              535              540 aaa taa gtaatctcta caaacagaaa tggcataaag ctgaagctgt atgtgtatct    1748
Lys ttacaaagta aattctacct aaaagagctc cgagttgtaa cttgtttgta tattttattt    1808
tttgaatgaa ggaagattta taagatcatg taatcactca tcaaagttta aatatcatca    1868
tttgtatcac tacattcggt ttttccgatc ataaacattg atttttcat gttaaaagt     1927
```

METHODS OF MODIFYING LIGNIN IN PLANTS BY TRANSFORMATION WITH A 4-COUMARATE COENZYME A LIGASE NUCLEIC ACID

STATEMENT OF GOVERNMENT RIGHTS

The present invention was made at least in part with the support of the United States Government via a grant from the U.S. Department of Agriculture (Grant No. 95-37103-2061). The Government may have certain rights in the invention.

FIELD OF THE INVENTION

The invention relates to genetically modifying trees through manipulation of the lignin biosynthesis pathway, and more particularly, to genetically modifying trees through the down regulation of p-coumarate Co-enzyme A ligase (CCL) to achieve faster growth, and/or altered lignin content, and/or altered lignin structure, and/or altered cellulose content and/or disease resistance of the trees and to the use of promoters of the CCL genes to drive gene expression specifically in xylem tissue or specifically in epidermal tissues.

BACKGROUND OF THE INVENTION

Genetic engineering of forest tree species to conform to desired traits has shifted the emphasis in forest tree improvement away from the traditional breeding programs during the past decade. Although research on genetic engineering of forest trees has been vigorous, the progress has been slow due.

The ability to make trees grow faster and be disease resistant to produce the highest volume of wood in the shortest period of time has been and continues to be the top objective of many forest products company worldwide. The ability to genetically increase the optimal growth of trees would be a commercially significant improvement. Faster growing trees could be used by all sectors of the forest and wood products industry worldwide.

Lignin, a complex phenolic polymer, is a major component in cell walls of secondary xylem. In general, lignin constitutes 25% of the dry weight of the wood, making it the second most abundant organic compound on earth after cellulose. Although lignin plays an important role in plants, it usually represents an obstacle to utilizing biomass in several applications. For example, in woodpulp production, lignin has to be removed through expensive and polluting processes in order to recover cellulose.

Thus, it is desirable to genetically engineer plants with reduced lignin content and/or altered lignin composition that can be utilized more efficiently. Trees that could be genetically engineered with a reduced amount of lignin would be commercially valuable. These genetically engineered trees would be less expensive to pulp because, in essence, part of the pulping has already been performed due to the reduced amount of lignin.

Trees with increased cellulose content would also be commercially valuable to the pulp and paper industry.

Disease resistance in plants is also a most desirable plant trait. The impact of disease resistance in trees on the economy of forest products industry worldwide is significant.

Promoters that target specific plant tissue could be useful in manipulating gene expression to enable the engineering of traits of interest in specific tissue of plants, such as, xylem and epidermal tissues.

Although studies have revealed several general properties of plant p-coumarate Co-enzyme A ligase (CCL), the role of CCL in regulating the synthesis of monolignols in response to different states of development and environmental stress in tree species remains largely unknown. Furthermore, multiple CCL isoforms are normally present in plants, channeling phenolic compounds to the biosynthesis of not only lignin but also other phenylpropanoids, such as flavonoids. Since CCL isoforms have not been previously cloned from tree species for the identification of their biochemical functions, the presence of CCL isoforms remains so far as a challenge to a specific control of metabolic flux to the lignin biosynthesis in tree species.

SUMMARY OF THE INVENTION

The invention provides a method to genetically alter trees through the down regulation of p-coumarate Co-enzyme A ligase (CCL). Such down regulation of CCL results in faster growth, and/or reduced lignin content, and/or altered lignin structure, and/or altered cellulose content and/or disease resistance. The invention also provides for genetically engineered trees which have been altered to down regulate p-coumarate Co-enzyme A ligase (CCL) to achieve faster growth, and/or reduced lignin content, and/or altered lignin structure, and/or increased cellulose content and/or increased disease resistance. The invention also provides tissue specific promoters of the CCL genes that can be used to manipulate gene expression in target tissue such as xylem and epidermal tissues.

It is one object of the present invention to down regulate p-coumarate Co-enzyme A ligase (CCL) in trees.

It is another object of the present invention to provide a method to genetically alter trees to grow faster.

It is another object of the present invention to provide a method to genetically alter the growth of trees through manipulation the lignin pathway p-coumarate Co-enzyme A ligase.

It is another object of the present invention to provide genetically altered trees with an accelerated growth characteristic.

It is another object of the present invention to provide transgenic trees with an accelerated growth characteristic which have been genetically altered by down regulating lignin pathway p-coumarate Co-enzyme A ligase.

It is another object of the present invention to provide a method to genetically alter trees to reduce their lignin content.

It is another object of the present invention to provide a method to genetically alter the lignin content of trees through manipulation of a lignin pathway enzyme.

It is another object of the present invention to genetically engineer trees which have reduced lignin content through manipulation of lignin pathway p-coumarate Co-enzyme A ligase.

It is another object of the present invention to provide genetically altered trees with a reduced lignin content.

It is another object of the present invention to provide transgenic trees with reduced lignin content which have been genetically altered by down regulating the p-coumarate Co-enzyme A ligase (CCL).

It is another object of the present invention to provide a method to genetically alter trees to change their lignin structure through manipulation of lignin pathway p-coumarate Co-enzyme A ligase.

It is another object of the present invention to provide trees with altered lignin structure.

It is another object of the present invention to provide a method to increase the cellulose content in trees.

It is another object of the present invention to provide a method to increase the cellulose content of trees through the manipulation of a lignin pathway enzyme.

It is another object of the present invention to provide trees with increased cellulose content.

It is another object of the present invention to provide transgenic trees having increased cellulose content from the down regulation of CCL.

It is another object of the present invention to provide a method to genetically alter trees to increase their disease resistance.

It is another object of the present invention to provide a method to genetically alter trees to be more disease resistant through manipulation of the lignin pathway p-coumarate Co-enzyme A ligase.

It is another object of the present invention to genetically alter trees to increase their disease resistance to fungal pathogens.

It is another object of the present invention to provide trees with increased disease resistance.

It is another object of the present invention to provide transgenic trees with increased disease resistance through down regulation of the lignin pathway p-coumarate Co-enzyme A ligase.

It is another object of the present invention to provide a method using a promoter of a CCL gene to target gene expression in specific plant tissue.

It is another object of the present invention to provide a method using a promoter of a CCL gene to target gene expression specifically in plant xylem.

It is another object of the present invention to provide a method using a promoter of the CCL gene to target gene expression specifically in the epidermal tissues of plants.

It is another object of the present invention to provide a CCL gene promoter that targets gene expression specifically in the xylem of plants.

It is another object of the present invention to provide a CCL gene promoter that targets gene expression specifically in the epidermal tissues of plants.

Other features and advantages of the invention will become apparent to those of ordinary skill in the art upon review of the following drawing, detailed description and claims.

Before one embodiment of the invention is explained in detail, it is to be understood that the invention is not limited in its application to the details set forth in the following description of the preferred embodiment. The invention is capable of other embodiments and of being practiced or being carried out in various ways. Also, it is to be understood that the phraseology and terminology used herein is for the purpose of description and should not be regarded as limiting.

DETAILED DESCRIPTION OF THE PREFERRED EMBODIMENT

The invention pertains to genetically down regulating a lignin pathway p-coumarate Co-enzyme A ligase (CCL). Trees which have been genetically transformed to down regulate CCL will hereafter be called transgenic trees. Such down regulation can result in faster growing trees. Such down regulation can result in a reduction in the lignin content of the trees and/or altered lignin structure. Such down regulation can result in increased cellulose content. Such down regulation can result in increased tree disease resistance. Further, by using a specific promoter of CCL, targeted tissue gene expression can be achieved in either the xylem or the epidermal tissues of the plant.

A. CCL

Figure 1:
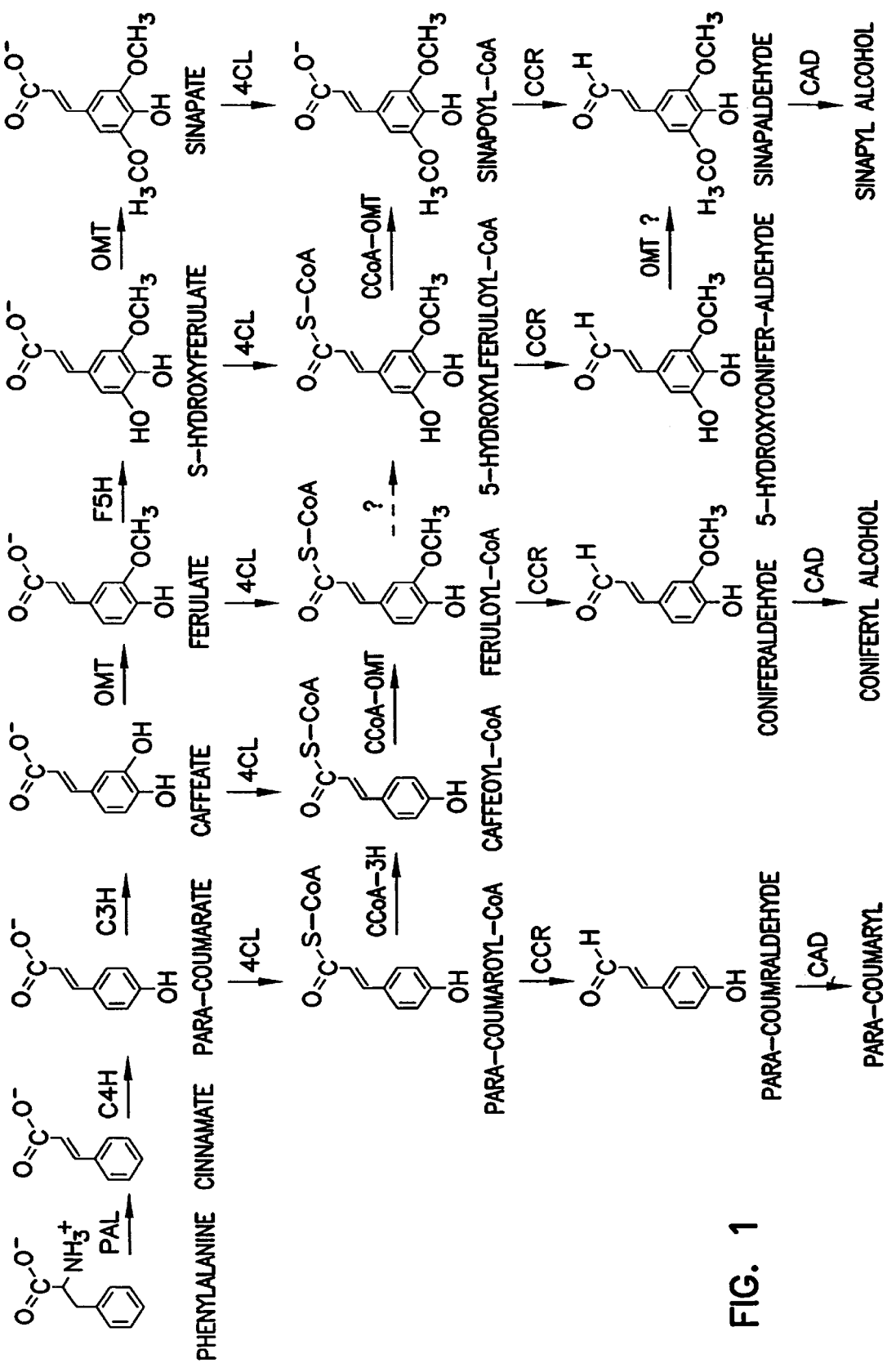
FIG. 1 is a schematic of a phenylpropanoid pathway.

Lignin is synthesized by the oxidative coupling of three monolignols (coumaryl, coniferyl and sinapyl alcohols) formed via the phenylpropanoid pathway as shown in FIG. 1. Reactions in the phenylpropanoid pathway include the deamination of phenylalanine to cinnamic acid followed by hydroxylations, methylations and activation of substituted cinnamic acids to coenzyme A (CoA) esters. The CoA esters are then reduced to form monolignols which are secreted from cells to form lignin.

The products of the phenylpropanoid pathway are not only required for the synthesis of lignin but also required for the synthesis of a wide range of aromatic compounds including flavonoids, phytoalexins, stilbenes and suberin.

In angiosperms (hardwoods), lignin is composed of both coniferyl and sinapyl alcohol and is classified as guaiacyl-syringyl lignin. Grasses synthesize a third precursor (p-coumaryl alcohol) which is polymerized along with coniferyl and sinapyl alcohol. In gymnosperms (softwoods), lignin is composed of mainly coniferyl alcohol and is classified as guaiacyl lignin.

In the phenylpropanoid pathway, CCL activates a number of cinnamic acid derivatives, including p-courmaric acid, caffeic acid, ferulic acid, 5-hydroxyferulic acid and sinapic acid. The resulting products, CoA esters, serve as substrates for entry into various branch pathways, such as lignin, flavonoids, phytoalexins, stilbenes and suberin. The esterification reactions catalyzed by CCL require high energy and the reactions are not likely to occur without CCL. CCL is important in making a continuous flow of the lignin biosynthesis pathway. CCL is also important because it is located at the branching points of the phenylpropanoid metabolism. CCL is suggested to play a pivotal role in regulating carbon flow into specific branch pathways of the phenylpropanoid metabolism in response to stages of development and environmental stress.

The basic properties of CCL are quite uniform. CCL depends on ATP as a cosubstrate and requires $Mg^{2+}$ as a cofactor. The optimal pH for CCL ranges from pH 7.0 to 8.5 and the molecular weight of CCL isoforms from various plant species ranges from 40 kd to 75 kd. Most CCLs have high affinity with substituted cinnamic acids. CCL has the highest activity with p-coumaric acid.

CCL cDNA sequences have been reported for parsley, potato, soybean, loblolly pine, Arabidopsis, Lithosperum and tobacco. CCL genes have been isolated and sequenced for parsley, rice, potato and loblolly pine. The analysis of CCL cDNAs and genes indicates that CCL is encoded by multiple/divergent genes in rice, soybean, and Lithosperum, very similar genes in parsley, potato, tobacco and loblolly pine, and a single gene in Arabidopsis. CCL promoters have been isolated and sequenced for parsley, rice and potato.

Alignment of deduced amino acid sequences of cloned plant CCL sequences reveals two highly conserved regions. The first conserved region (SSGTTGLPKGV)(SEQ ID NO:7), proposed to designate a putative AMP-binding region, is very rich in Gly, Ser and Thr and is followed by a conserved Lys. The second conserved region (GEICIRG) (SEQ ID NO:8) contains one common Cys residue. The amino acid sequences of CCL from plants contain a total of five conserved Cys residues.

The CCL genes of parsley, potato and rice contain five exons and four introns. The CCL genes also share the same exon/intron splice junction sites but have different lengths of introns. The genomic sequences of loblolly pine CCL are composed of four exons and three introns. It has been found that two similar CCL genes of the same species may differ slightly in length of intron as shown in two parsley genes (PC4CL1 and PC4CL2) and in two loblolly pine genes (LP4CL1 and LP4CL2).

By Northern blot analysis, it has been shown that CCL is expressed in leaf, shoot tip, stem, root, flower and cell culture. Two similar CCL cDNAs in parsley, potato and tobacco have been shown to be expressed at similar level in response to the environmental stress and during different developmental stages. Two distinct CCL cDNAs in soybean and Lithosperum have shown different expression levels when pathogens or chemicals were applied to the cell cultures. It appears that the expression of the CCL genes is developmentally regulated and inducible by many environmental stresses at the transcription level.

Genetic transformation with a CCL sequence can result in several significant affects. The description of the invention hereafter refers to aspen, and in particular quaking aspen (*Populus tremuloides* Michx) when necessary for the sake of example. However, it should be noted that the invention is not limited to genetic transformation of aspen. The method of the present invention is capable of being practiced for other trees, including for example, other angiosperms, other gymnosperm forest tree species, etc.

Preferably, the CCL down regulation is accomplished through transformation with a homologous CCL sequence in an antisense orientation. However, it should be noted that a heterologous antisense CCL sequence could be utilized and incorporated into a tree species to down regulate CCL if the heterologous CCL gene sequence has a high nucleotide sequence homology, approximately higher than 70%, to the endogenous CCL gene sequence of that tree species.

In addition, trees transformed with a sense CCL sequence could also cause a sequence homology-based cosuppression of the expression of the transgene and endogenous CCL gene, thereby achieving down regulation of CCL in these trees.

B. Isolation of CCL cDNAs

The present invention utilizes a homologous CCL sequence to genetically alter trees. The preferred embodiment of the invention as further described below utilizes a cDNA clone of the quaking aspen CCL gene.

Two aspen (*Populus tremuloides* Michx) cDNAs encoding two distinct CCL isoforms, PtCCL1and PtCCL2 have been cloned. PtCCL1 cDNA is lignin pathway-specific and is different from PtCCL2 cDNA, which is involved in flavonoid synthesis. The cloning of PtCCL1 and PtCCL2 cDNAs and the identification of their biochemical functions will be discussed in more length below. PtCCL1 and PtCCL2 genomic clones including their 5'-end regulatory promoter sequences were also isolated. The promoter of PtCCL1 (PtCCL1p) directs xylem tissue-specific gene expression in a plant, whereas the promoter of PtCCL2 (PtCCL2p) drives the expression of genes specifically in epidermal tissues of stem and leaf of a plant. These tissue specific promoters will be discussed in more length in Section I below.

Two CCL cDNAs, PtCCL1 and PtCCL2, have been isolated from quaking aspen using either a conventional cDNA library screening method or a PCR-based cDNA cloning method. It should be noted that the methods described below are set forth as an example and should not be considered limiting. These CCL cDNA clones are available from Michigan Technological University, Institute of Wood Research, Houghton, Mich.

Young leaves and shoot tips are collected from greenhouse-grown quaking aspen (*Populus tremuloides* Michx). Differentiating xylem and sclerenchyma are collected from three to four year old quaking aspen. The bark is peeled from the tree exposing the developing secondary xylem on the woody stem and the sclerenchyma on the inner side of the bark. Developing secondary xylem and sclerenchyma are scraped from the stem and bark with a razor blade and immediately frozen in liquid nitrogen until use.

Total RNA is isolated from the young leaves, shoot tips, xylem and sclerenchyma following the method of Bugos RC et al. (1995), RNA Isolation from Plant Tissue Recalcitrant to Extraction in Guanidine, Biotechniques 19(5):734–737. Poly(A)$^+$RNA is purified from total RNA using Poly(A)$^+$ mRNA Isolation Kit from Tel-test B. Inc. A unidirectional Lambda gt22 expression cDNA library was constructed from the xylem mRNA using Superscript $\lambda$ System from Life Technologies, Inc. and Gigapack Packaging Extracts from Stratagene. The PtCCL1 cDNA was obtained by screening the cDNA library with a $^{32}$P-labeled parsley 4CL cDNA probe. The parsley 4CL cDNA (pc4CL2) has Genbank accession number X13325(SEQ ID NO:15).

The PtCCL2 cDNA was obtained by RT-PCR. The reverse transcription of total RNA isolated from shoot tips was carried our using the Superscript II reverse transcriptase from Life Technologies. Two sense primers (R1S, 5'-TTGGATCCGGIACIACIGGIYTICCIAARGG-3'(SEQ ID NO:9) and H1S, 5'-TTGGATCCGTIGCICARCARGTIGAYGG-3')(SEQ ID NO:10) are designed around the first consensus AMP-binding region of CCL that was previously discussed. One antisense primer (R2A, 5'-ATGTCGACCICGDATRCADATYTCICC-3')(SEQ ID NO:11) is designed based on the sequence of the putative catalytic motif GEICIRG(SEQ ID NO:8). One fifth of the reverse transcription reaction (4 $\mu$l) is used as the template in a 50 $\mu$l PCR reaction containing 1× reaction buffer, 200 $\mu$M each deoxyribonucleotide triphosphate, 2 $\mu$M each R1S and oligo-dT (20 mer) primers, and 2.5 units of Taq DNA polymerase. The PCR reaction mixture was denatured at 94° C. for 5 minutes followed by 30 cycles of 94° C./45 seconds, 50° C./1 minute, 72° C./90 seconds and is ended with a 5 minute extension at 72° C. 2 $\mu$l of the PCR amplification products are used for a second run PCR re-amplification using primers H1S and R2A. A 0.6 kb PCR fragment is cloned using the TA Cloning Kit from Invitrogen and used as a probe to screen an aspen genomic library to obtain the PtCCL2 genomic clone. Two primers (2A, 5'-TCTGTCTAGATGATGTCGTGGCCACGG-3'(SEQ ID NO:12) and 2B, 5'-TTAGATCTCTAGGACATGGTGGTGGC-3')(SEQ ID NO:13) are designed based on the genomic sequence of PtCCL2 at around the deduced transcription start site and stop codon for the cloning of PtCCL2 cDNA by RT-PCR as described above using total RNA isolated from shoot tips.

The DNA sequences of PtCCL1 and PtCCL2 cDNA were determined using ΔTaq Cycle Sequencing Kit from Amersham.

The PtCCL1 cDNA has an open reading frame of 1620 bp which encodes a polypeptide of 540 amino acid residues with a predicted molecular weight of 59 kd and pI of 5.8. The nucleotide sequence of the aspen CCL cDNA clone PtCCL1 is set forth as SEQ ID NO:1. The deduced amono acid sequence for the aspen CCL1 protein is set forth as SEQ ID NO:2.

The PtCCL2 cDNA has an open reading frame of 1713 bp which encodes a polypeptide of 571 amino acid residues with a predicted molecular weight of 61.8 kd and pI of 5.1. The nucleotide sequence of the aspen CCL cDNA clone PtCCL2 is set forth as SEQ ID NO:3. The deduced amino acid sequence for the aspen CCL2 protein is set forth as SEQ ID NO:4.

The aspen PtCCL1 cDNA shares a 59–74% identity at the nucleotide level and 59–81% identity at the amino acid level with other prior reported CCL cDNAs and genes, whereas the PtCCL2 cDNA shares a 60–73% identity at the nucleotide level and 57–74% at the amino acid level with other CCL cDNAs and genes as set forth in the following table.

TABLE 1

Comparison of PtCCL1 and PtCCL2 Nucleotide and Predicted Amino Acid Sequence to Each Other and Other CCL Sequences

| cDNA* | DNA IDENTITY % PtCCL1 | DNA IDENTITY % PtCCL2 | AMINO ACID IDENTITY % PtCCL1 | AMINO ACID IDENTITY % PtCCL2 |
|---|---|---|---|---|
| PtCCL1 |  | 62 |  | 63 |
| LE4CL1 | 69 | 62 | 71 | 64 |
| LE4CL2 | 60 | 71 | 59 | 73 |
| GM14 | 74 | 67 | 81 | 69 |
| GM16 | 62 | 73 | 65 | 73 |
| NT4CL1 | 67 | 62 | 75 | 74 |
| NT4CL2 | 66 | 63 | 75 | 66 |
| PC4CL1 | 66 | 64 | 71 | 64 |
| PC4CL2 | 66 | 63 | 72 | 64 |
| ST4CL1 | 67 | 63 | 75 | 64 |
| AT4CL | 66 | 63 | 70 | 61 |
| LP4CL | 61 | 64 | 63 | 67 |
| OS4CL1 | 59 | 60 | 59 | 57 |

*PtCCL1: aspen CCL
PtCCL2: aspen CCL
LE4CL1 and LE4CL2: *Lithosperum erythrorhizon* CCL
GM14 and GM16: soybean CCL
NT4CL1 and NT4CL2: tobacco CCL
PC4CL1 and PC4CL2: parsley CCL
ST4CL1: potato CCL
AT4CL: Arabidopsis CCL
LP4CL: loblolly pine CCL
OS4CL1: rice CCL The results of sequence analysis, phylogenetic tree and genomic Southern blot analysis indicate that PtCCL1 and PtCCL2 cDNAs encode two distinct CCLs that belong to two divergent gene families in aspen. The deduced amino acid sequence for the PtCCL2 protein contains a longer N-terminal sequence than the PtCCL1 protein but shows profound similarity in the central and C-terminal portions of protein to the PtCCL1 protein.

PtCCL1 and PtCCL2 cDNAs display distinct tissue-specific expression patterns. The PtCCL1 sequence is expressed highly in the secondary developing xylem and in the 6th to 10th internodes whereas the PtCCL2 sequence is expressed in the shoot tip and leaves. These tissue-specific expression patterns were investigated by fusing promoters of PtCCL1 and PtCCL2 genes to a GUS reporter gene. The tissue specific promoters for PtCCL1 and PtCCL2 will be discussed in more length in Section I below.

The substrate specificity of PtCCL1 and PtCCL2 is also different from each other as determined using recombinant proteins produced in *E. coli*. PtCCL1 utilized p-coumaric acid, caffeic acid, ferulic acid and 5-hydroxyferulic acid as substrates. PtCCL2 showed activity to p-coumaric acid, caffeic acid and ferulic acid but not to 5-hydroxyferulic acid.

Specifically, PtCCl1 and PtCCL2 were used to construct expression vectors for *E. coli* expression. The substrate specificity of PtCCL1 and PtCCL2 were tested using fusion proteins produced in *E. coli*. Two plasmids, pQE/CCL1 and pQE/CCL2, were constructed in which the coding regions of PtCCL1 and PtCCL2, respectively were fused to N-terminal His tags in expression plasmids pQE-31 and pQE-32 (QIAGEN, Chatsworth, Calif). The recombinant proteins of PtCCL1 and PtCCL2 produced by *E. coli* are approximately 59 kd and 63 kd, respectively.

The two recombinant proteins were tested for their activity in utilizing cinnamic acid derivatives. PtCCL1 recombinant protein showed 100, 58, 71, 18 and 0% relative activity to p-coumaric acid, caffeic acid, ferulic acid, 5-hydroxyferulic acid and sinapic acid, respectively. PtCCL2 recombinant protein exhibited 100, 14, 27, 0 and 0% relative activity to p-coumaric acid, caffeic acid, ferulic acid, 5-hydroxyferulic acid and sinapic acid, respectively. Neither recombinant protein showed detectable activity to sinapic acid.

The results of the tissue-specific expression pattern and substrate specificity suggests that in addition to the general function of CCL, PtCCL1 apparently is more related to lignin synthesis in the xylem tissue and PtCCL2 apparently is more likely involved in flavonoid synthesis and UV protection.

It should be noted that the isolation and characterization of the PtCCL1 and PtCCL2 cDNA clones is described in Kawaoka A, Chiang V L (1995), The Molecular Cloning and Expression of Syringyl- and Guaiacyl-Specific Hydroxycinnamate:CoA Ligases from Aspen (*Populus tremuloides*), Proceedings of the 6th International Conference on Biotechnology in the Pulp and Paper Industry, Vienna, Austria; and in Hu, Wen-Jing, Isolation and Characterization of p-coumarate Co-enzyme A ligase cDNAs and Genes from Quaking Aspen (*Populous tremuloides* Michx), Ph.D Dissertation, Michigan Technological University, Houghton, Mich. (1997); which are both herein incorporated by reference.

C. Transformation and Regeneration

Several methods for gene transformation of plant species with the CCL sequence are available such as the use of a transformation vector, agroinfection, electroinjection, particle bombardment with a gene gun or microinjection.

Preferably, a CCL cDNA clone is positioned in a binary expression vector in an antisense orientation under the control of double cauliflower mosiac virus 35S promoter.

The vector is then preferably mobilized into a strain of Agrobacterium species such as tumefaciens strain C58/pMP90 and is used as the DNA delivery system due to its efficiency and low cost.

Figure 2:
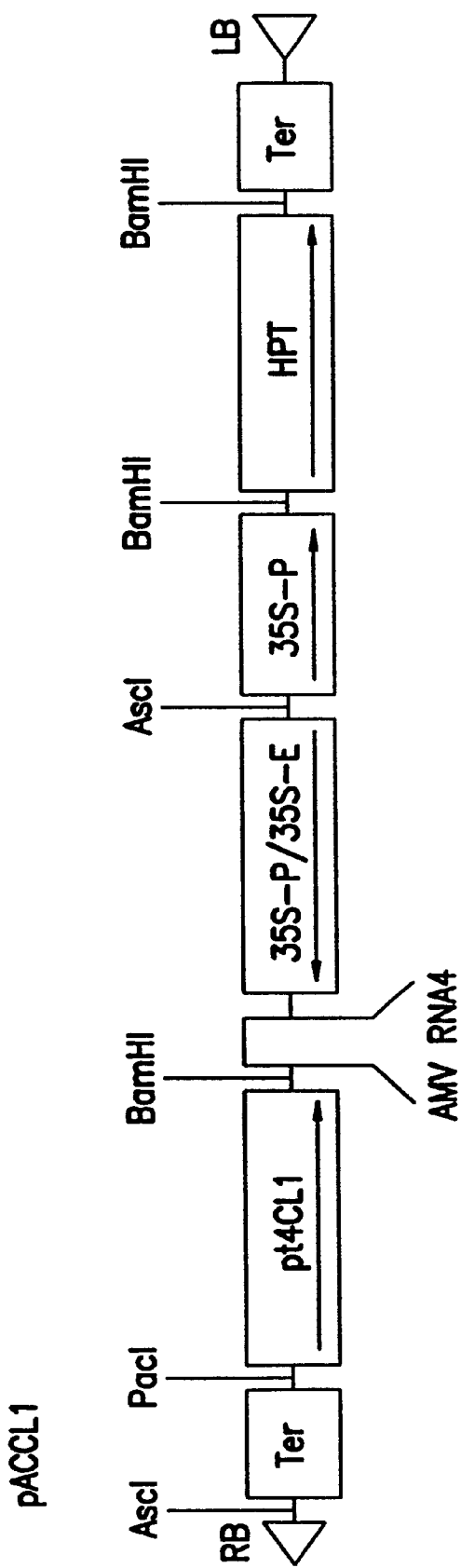
FIG. 2 is a diagram of Agrobacterium T-DNA construct pACCL1.

For example, with reference to FIG. 2, the binary expression pACCL1 used for plant transformations is shown. Specifically, the PtCCL1 CDNA is inserted in an antisense orientation into Pac I and BamH I sites between the double CaMV 35S/AMV RNA4 and the 3' terminator sequence of the nopaline synthase gene in a binary cloning vector pACCL1(FIG. 2). The binary vector containing hygromycin phosphotransferase (HPT) gene is modified from pBin 19.

The gene construct pACCL1is available from Michigan Technological University, Institute of Wood Research, Houghton, Mich.

The binary vector construct is mobilized in *Agrobacterium tumefaciens* using the freeze-thaw method of Holsters et al., Mol. Gen. Genet. 163:181–187 (1978). For the freeze-thaw method, 1.5 ml of overnight cultures *Agrobacterium tumefaciens* strain C58/pMP90 is pelleted at 5000×g for 3 minutes at 4° C. and suspended in 1 ml of ice cold 20 mM $CaCl_2$. To the suspension is added 10 μl binary vector DNA (from an alkaline lysis minipreparation) and mixed by pipetting. The microcentrifuge tube is then frozen in liquid nitrogen for 5 minutes and thawed at 37° C. for 5 minutes. After being cooled on ice, 1 ml of LB is added and the mixture is incubated at 28° C. for 2 hours with gentle shaking. 200 pl of the cells is spread onto LB plates containing gentamycin and kanamycin and incubated at 28° C. for 2 days. Colonies grown on the selection plates are randomly picked or miniprep and restriction enzyme digestion analysis is used to verify the integration.

The resulting binary vector containing Agrobacterium strain is used to transform quaking aspen according to Tsai et al., Agrobacterium-Mediated Transformation of Quaking Aspen (*Populous tremuloides*) and Regeneration of Transgenic Plants, Plant Cell Rep. 14:94–97 as set forth below.

Explants of young leaves from cuttings of aspen are obtained by cutting leaf disks of approximately 7 mm square from the young leaves along the midrib of the leaves. The explants are surface sterilized in 20% commercial bleach for 10 minutes followed by rinsing 3 times with sterile double-distilled water.

All of the culture media used includes the basal medium of woody plant medium (WPM) as described in Lloyd et al., Proc. Int. Plant Prop. Soc. 30:421–437 (1980) and supplemented with 2% sucrose. 650 mg/L calcium gluconate and 500 mg/L MES are added as pH buffers as described in Tsai, Plant Cell Reports, 1994. All culture media is adjusted to pH 5.5 prior to the addition of 0.075% Difco Bacto Agar and then autoclaved at 121° C. and 15 psi for 20 minutes. Filter sterilized antibiotics are added to all culture media after autoclaving. All culture media are maintained at 23±1° C. in a growth chamber with 16 hour photoperiods (160 $\mu E \times m^{-2} \times S^{-1}$) except for callus induction (as will be described later) which is maintained in the dark.

The sterilized explants are then inoculated with the mobilized vector with an overnight-grown agrobacterial suspension containing 20 μM acetosyringone. After cocultivation for 2 days, the explants are washed in 1 mg/ml claforan and ticarcillin for 2 hours with shaking to kill Agrobacterium. The explants are blotted dry with sterile Whatman No. 1 filter paper and transferred onto callus induction medium containing 50 mg/L kanamycin and 300 mg/L claforan to induce and select transformed callus. The callus induction medium is the basal medium with the addition of 6-benzyladenine (BA) and 2,4-dichlorophenoxyacetic acid (2,4-D) at concentrations of 0.5 mg/L and 1 mg/L, respectively, to induce callus.

The kanamycin-resistant explants are then subcultured on fresh callus induction media every two weeks. Callus formation occurs after approximately four weeks. Formed callus are separated from the explant and subcultured periodically for further proliferation.

When the callus clumps reach approximately 3 mm in diameter, the callus clumps are transferred to shoot regeneration medium. The shoot regeneration medium is the basal medium containing 50 mg/L kanamycin, 0.5 mg/L thidiazuron (TDZ) as a plant growth regulator and cefotaxime at 300 mg/L to kill Agrobacterium. Shoots were regenerated about 4 weeks after callus is transferred to regeneration medium.

As soon as the shoots are regenerated, they are immediately transferred to hormone-free elongation medium containing 50 mg/L kanamycin and, whenever necessary, cefotaxime (300 mg/L), to promote elongation. Green and healthy shoots elongated to 2–3 cm in length are excised and planted separately in a hormone-free rooting medium containing 50 mg/L kanamycin. The efficient uptake of kanamycin by shoots during their rooting stage provides the most effective selection for positive transformants. Transgenic plants are then transplanted into soil medium of vermiculite:peatmoss:perlite at 1:1:1 and grown in the greenhouse.

The above described transformation and regeneration protocol is readily adaptable to other tree species. Other published transformation and regeneration protocols for tree species include Danekar et al., Bio/Technology 5:587–590 (1987); McGranahan et al., Bio/Technology 6:800–804 (1988); McGranahan et al., Plant Cell Reports 8:512–616 (1990); Chen, phD Thesis, North Carolina State University, Raleigh, N.C. (1991); Sullivan et al., Plant Cell Reports 12:303–306 (1993); Huang et al., In Vitro Cell Dev. Bio. 4:201–207 (1991); Wilde et al., Plant Physiol. 98:114–120 (1992); Minocha et al., 1986 Proc. TAPPI Research and Development Conference, TAPPI Press, Atlanta, pp. 89–91 (1986); Parsons et al., Bio/Technology 4:533–536 (1986); Fillatti et al., Mol. Gen. Genet 206:192–199 (1987); Pythoud et al., Bio/Technology 5:1323–1327 (1987); De Block, Plant Physiol. 93:1110–1116 (1990); Brasileiro et al., Plant Mol. Bio 17:441–452 (1991); Brasileiro et al., Transgenic Res. 1:133–141 (1992); Howe et al., Woody Plant Biotech., Plenum Press, New York, pp.283–294 (1991); Klopfenstein et al., Can. J. For. Res. 21:1321–1328 (1991); Leple et al., Plant Cell Reports 11:137–141 (1992); and Nilsson et al. Transgenic Res. 1:209–220 (1992).

D. Phenotype Changes

The results of the transformation can be confirmed with conventional PCR and Southern analysis. For example, transferring CCL CDNA in an antisense orientation down regulates CCL in the tree. Expression of the CCL has been found to be blocked up to 96 percent in some transgenic trees.

After acclimation, the transgenic aspen display an unusual phenotype, including big curly leaves, thick diameters, longer internodes, more young leaves in the shoot tip and a red pigmentation in the petioles extending into midvein leaves. Red coloration of the developing secondary xylem tissues is observed after peeling of the bark in the transgenic plants.

E. Accelerated Growth

Down regulation of CCL alters growth of the transgenic trees. For example, transformation with an antisense CCL sequence accelerates the growth of the tree. Enhanced growth is markedly noticeable at all ages. In particular, the transgenic trees show enhanced growth in the form of thicker stems and enlarged leaves as compared to control trees. These characteristics are retained in the vegetative propagules of these transgenic trees. Table 2 sets forth exemplary data with respect to several lines of transgenic quaking aspen grown in the greenhouse after eight months. Volume represents the overall quantitative growth of the tree.

TABLE 2

Growth Measurement for Control and Transgenic Plants

| PLANT # | HEIGHT (cm) | DIAMETER (cm)* | VOLUME $(cm^3)$* | AVERAGE LENGTH OF INTERNODE (cm) |
|---|---|---|---|---|
| Control 1 | 247.7 | 1.08 | 75.6 | 2.6 |
| Control 2 | 250.2 | 1.01 | 66.8 | 2.8 |
| 11-1 | 304.8 | 1.15 | 105.5 | 3.1 |
| 11-2 | 248.9 | 1.01 | 66.4 | 3.4 |
| 11-3 | 241.3 | 0.84 | 44.6 | 3.2 |
| 11-4 | 288.3 | 0.94 | 66.7 | 3.4 |
| 11-5 | 246.4 | 0.92 | 54.6 | 3.3 |
| 11-7 | 226.7 | 1.13 | 75.7 | 3.4 |
| 11-8 | 289.6 | 1.16 | 102.0 | 3.3 |
| 11-9 | 287.0 | 1.76 | 232.6 | 4.3 |
| 11-10 | 252.7 | 0.83 | 45.6 | 3.1 |
| 11-11 | 247.7 | 0.86 | 48.0 | 3.5 |
| 12-1 | 247.7 | 1.1 | 78.4 | 2.7 |
| 12-2 | 199.4 | 0.96 | 48.1 | 2.5 |
| 12-6 | 294.6 | 0.92 | 65.2 | 3.2 |
| 16-1 | 227.3 | 0.95 | 53.7 | 2.8 |
| 16-2 | 278.1 | 0.97 | 68.5 | 3.4 |
| 16-3 | 265.4 | 1.09 | 82.5 | 3.5 |
| 17-2 | 243.8 | 0.89 | 50.5 | 2.6 |

*at 10 cm above ground

The averages for height, diameter, volume and average length between internodes for the control plants are as follows:

| Height (cm) | 248.95 |
|---|---|
| Diameter (cm) | 1.045 |
| Volume $(cm^3)$ | 71.2 |
| Ave. Length of Internodes (cm) | 2.7 |

With respect to height alone, for those transgenic plants (11-1, 11-4, 11-8, 11-9, 12-6, 16-2, 16-3) having a statistically larger height than the control plants, the average height was 286.83 cm as compared to the control plant average height of 248.95 cm.

With respect to diameter alone, for those transgenic plants (11-1, 11-7, 11-8, 11-9) having a statistically larger diameter than the control plants, the average diameter was 1.30 cm as compared to the control plant average diameter of 1.045 cm.

With respect to volume alone, for those transgenic plants (11-1, 11-8, 11-9, 12-1, 16-3) having a statistically larger volume than the control plants, the average volume was 120.2 $cm^3$ as compared to the control plant average volume of 71.2 $cm^3$.

With respect to average length of internodes alone, for those transgenic plants (11-1, 11-2, 11-3, 11-4, 11-5, 11-7, 11-8, 11-9, 11-10, 12-6, 16-2, 16-3) having a statistically larger average length of internodes than the control plants, the average average length of internodes was 3.39 cm as compared to the control plant average average length of internodes of 2.7° cm.

As demonstrated in Table 2, while there are variations in growth among the transgenic trees, the average length of the internodes for the transgenic trees is consistently and significantly higher than that of the control plants. Variations in the growth of the transgenic trees is normal and to be expected. Preferably, a transgenic tree with a particular growth rate is selected and this tree is vegetatively propagated to produce an unlimited number of clones that all exhibit the identical growth rate.

F. Lignin

Down regulation of lignin pathway CCL results in production of trees with reduced lignin content.

The following table shows the reduction of lignin content and CCL enzyme activity in several transgenic aspen which have been transformed with an homologous antisense CCL sequence.

TABLE 3

Characterization of Transgenic Aspen Plants Harboring Antisense CCL Sequence

| Transgenic Plant # | Lignin Content % Based On Wood Weight | % Lignin Reduction | CCL Enzyme Activity* | % CCL Enzyme Activity Reduction |
|---|---|---|---|---|
| control | 21.4 | 0.0 | 868 | 0 |
| 11-1 | 20.5 | 4.2 | 1171 | −25 |
| 11-2 | 19.2 | 10.3 | 515 | 45 |
| 11-3 | 20.9 | 2.3 | 922 | 6 |
| 11-4 | 19.7 | 7.9 | 1032 | −19 |
| 11-5 | 19.7 | 7.9 | 691 | 20 |
| 11-7 | 19.9 | 7.0 | 578 | 38 |
| 11-8 | 20.2 | 5.6 | 694 | 20 |
| 11-9 | 20.4 | 4.7 | 806 | 14 |
| 11-10 | 19.4 | 9.3 | 455 | 51 |
| 11-11 | 20.4 | 4.7 | 726 | 22 |
| 12-1 | 12.8 | 40.2 | 49 | 95 |
| 12-2 | 12.6 | 41.1 | 62 | 93 |
| 12-3 | 11.9 | 44.4 | 61 | 94 |
| 12-6 | 19.8 | 7.5 | 786 | 16 |
| 16-1 | 12.8 | 40.2 | 35 | 96 |
| 16-2 | 20.6 | 3.7 | 780 | 17 |
| 16-3 | 21.0 | 1.9 | 795 | 15 |
| 17-1 | 20.5 | 4.2 | 855 | 9 |
| 17-2 | 21.4 | 0.0 | 925 | 1 |

*activity is expressed as pkat/(mg protein) using p-coumaric acid as the substrate Lignin content was determined according to Chiang and Funaoka (1990) Holzforschung 44:147–155. CCL enzyme activity was determined according to Ranjeva et al. (1976), Biochimie 58:1255–1262.

The data in Table 3 demonstrates a correlation between down regulation of CCL and reduction in lignin content.

Transgenic trees with reduced lignin content have an altered phenotype in that the stem is more elastic to the touch and the leaves are typically curlier.

It should also be noted that for those transgenic trees (12-1, 12-2, 12-3 and 16-1) with the approximately 40% reduction in lignin content and the corresponding approximately 95% reduction in CCL enzyme levels, all of those transgenic trees had a consistent deep red coloration in the wood of the plant. Accordingly, the deep red color can be used as an identifier of reduced lignin content.

Down regulation of lignin pathway CCL also results in production of trees with an altered lignin structure. Based upon thioacidolysis (Rolando et al. (1992) Thioacidolysis, Methods in Lignin Chemistry, Springer-Verlag, Berlin, pp 334–349) of plants 12-3 and 16-1, coniferyl alcohol and sinapyl alcohol lignin units are significantly reduced in these two trees as compared to the control tree, as shown in the following table.

TABLE 4

Altered Lignin Structure

| Plant # | Coniferyl Alcohol Units* | Sinapyl Alcohol Units* |
|---|---|---|
| control | 733 | 1700 |
| 12-3 | 283 | 592 |
| 16-1 | 247 | 445 |

*micro-mole/g of lignin

The alteration of the frequency of the structural units in lignin of these transgenic trees is evidence that the overall structure of lignin in these plants has been genetically altered.

G. Cellulose Content

Down regulation of lignin pathway CCL results in increased cellulose content of the transgenic plants. Analysis of control and transgenic aspen for carbohydrate content demonstrate a higher cellulose content in the transgenic trees than the control trees. Particularly, the transgenic trees that have over 40% lignin reduction have about 10–15% higher cellulose content than the control. Data is set forth in the following tables for trees that were transformed with homologous CCL in an antisense orientation:

TABLE 5

Analysis of Carbohydrate Components in Transgenic and Control Aspen

| Plant # | Glucan | Arabinan | Galactan | Rhamnan | Xylan | Mannan |
|---|---|---|---|---|---|---|
| Control | 44.23% | 0.47% | 0.79% | 0.37% | 17.19% | 1.91% |
| 11-2 | 49.05% | 0.36% | 1.05% | 0.38% | 15.34% | 2.04% |
| 11-9 | 45.95% | 0.40% | 0.80% | 0.37% | 17.12% | 1.83% |
| 11-10 | 47.49% | 0.43% | 0.99% | 0.40% | 16.24% | 2.35% |
| 12-3 | 50.83% | 0.55% | 1.24% | 0.48% | 17.25% | 1.77% |
| 16-1 | 48.14% | 0.56% | 1.07% | 0.48% | 19.14% | 1.58% |
| 16-2 | 46.55% | 0.34% | 0.82% | 0.37% | 16.75% | 2.31% |

TABLE 6

Comparison of Lignin and Cellulose (glucan) Contents in Transgenic and Control Aspen

| | Lignin | | Cellulose | |
|---|---|---|---|---|
| Plant # | Content % on wood | % reduction | Content % on wood | % increase |
| Control | 21.4 | 0 | 44.23 | 0 |
| 11-2 | 19.2 | 10.3 | 49.05 | 11.0 |
| 11-9 | 20.4 | 4.7 | 45.95 | 3.9 |
| 11-10 | 19.4 | 9.3 | 47.49 | 7.4 |
| 12-3 | 11.9 | 44.5 | 50.83 | 15.0 |
| 16-1 | 12.8 | 40.2 | 48.14 | 6.8 |
| 16-2 | 20.6 | 3.7 | 46.55 | 5.2 |

The procedure for carbohydrate analysis utilized is as follows. About 100 mg of powdery woody tissue with sizes that pass a 80-mesh screen was hydrolyzed with 1 mL of 72% (W/W) H2SO4 for 1 hr at 30° C. Samples were then diluted to 4% (W/W) H2SO4 with distilled water, fucose was added as an internal standard, and a secondary hydrolysis was performed for 1 hr at 121° C. After secondary hydrolysis, the sugar contents of the hydrolysates are determined by anion exchange high performance liquid chromatography using pulsed amperometric detection. Sugar contents are expressed as % of the weight of the woody tissue used. The above procedures are similar to those in a publication by RC Pettersen and VH Schwandt, 1991, J. Wood Chem & Technol. 11:495–501.

H. Increased Disease Resistance

Down regulation of lignin pathway CCL results in production of trees with increased disease resistance, and in particular, with increased fungal pathogen resistance.

In particular, greenhouse transgenic aspen plants showed a disease resistance to fungi such as those which induce leaf-blight disease.

I. Promoters

Two distinct genes encoding CCL and their promoters were cloned. The promoter of PtCCL1 can drive gene expression specifically in xylem tissue and the promotor for PtCCL2 confers gene expression exclusively in the epidermal tissues. These promoters can be used to manipulate gene expression to engineer traits of interest in specific tissues of target plants. The significance of the promoters is the application of the xylem-specific promoter to direct the expression of any relevant genes specifically in the xylem for engineering lignin content, lignin structure, enhanced tree growth, cellulose content and other value-added wood qualities, etc. The importance of the epidermis-specific promoter is its ability to drive the expression of any relevant genes specifically in epidermal tissues for engineering disease-, UV light-, cold-, heat-, drought-, and other stress resistance traits in trees.

Figure 3:
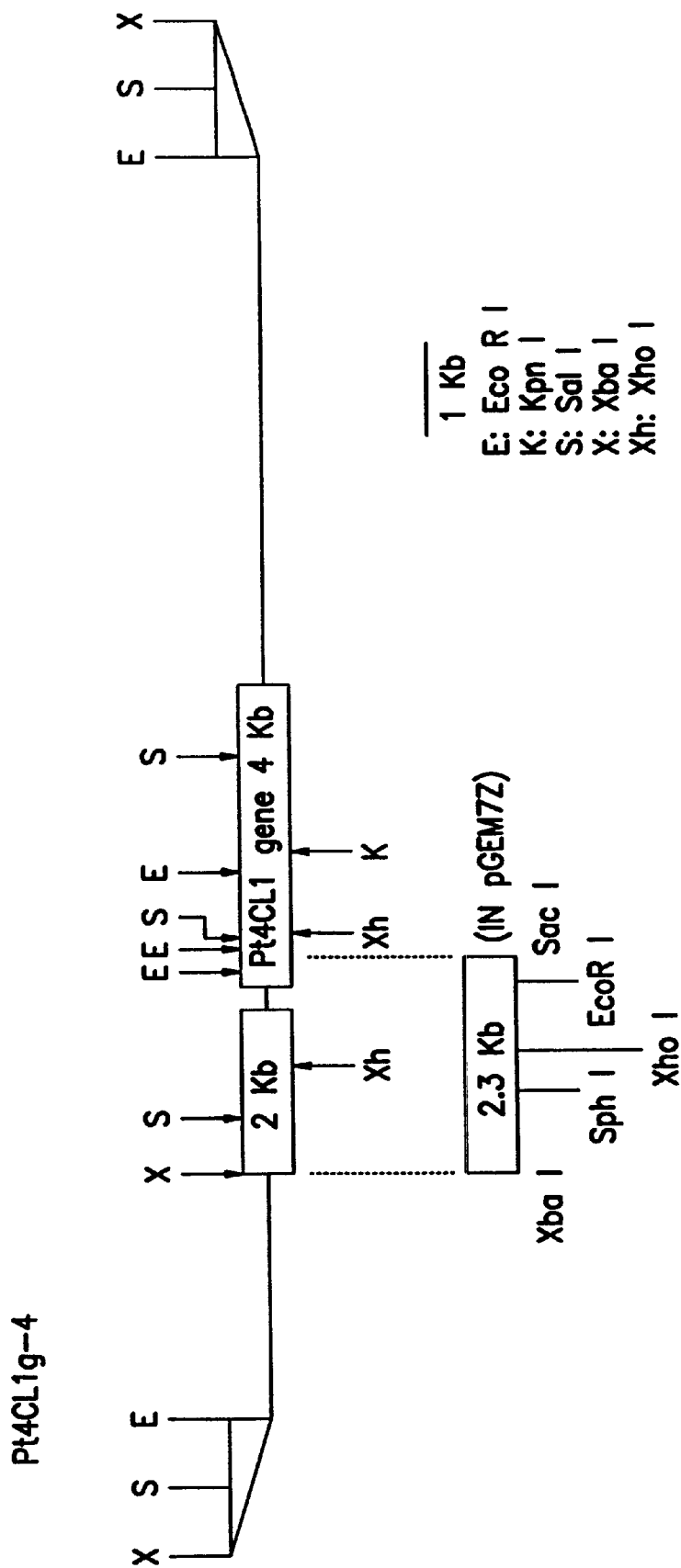
FIG. 3 is a restriction map of genomic clone PtCCL1g-4.

Specifically, the promoters of the PtCCL1 and PtCCL2 were conventionally isolated as follows. An aspen genomic library was screened with PtCCL1cDNA and PtCCL2 partial cDNA fragment to isolate genomic clones of PtCCL1 and PtCCL2. Eleven and seven positive genomic clones were identified for PtCCL1 and PtCCl2 gene, respectively. Among 11 positive clones for PtCCL1, PtCCL1g-4 contained a full length coding sequence and at least 2 kb 5' flanking regions. The restriction map of PtCCL1g-4 is set forth at FIG. 3.

Figure 4:
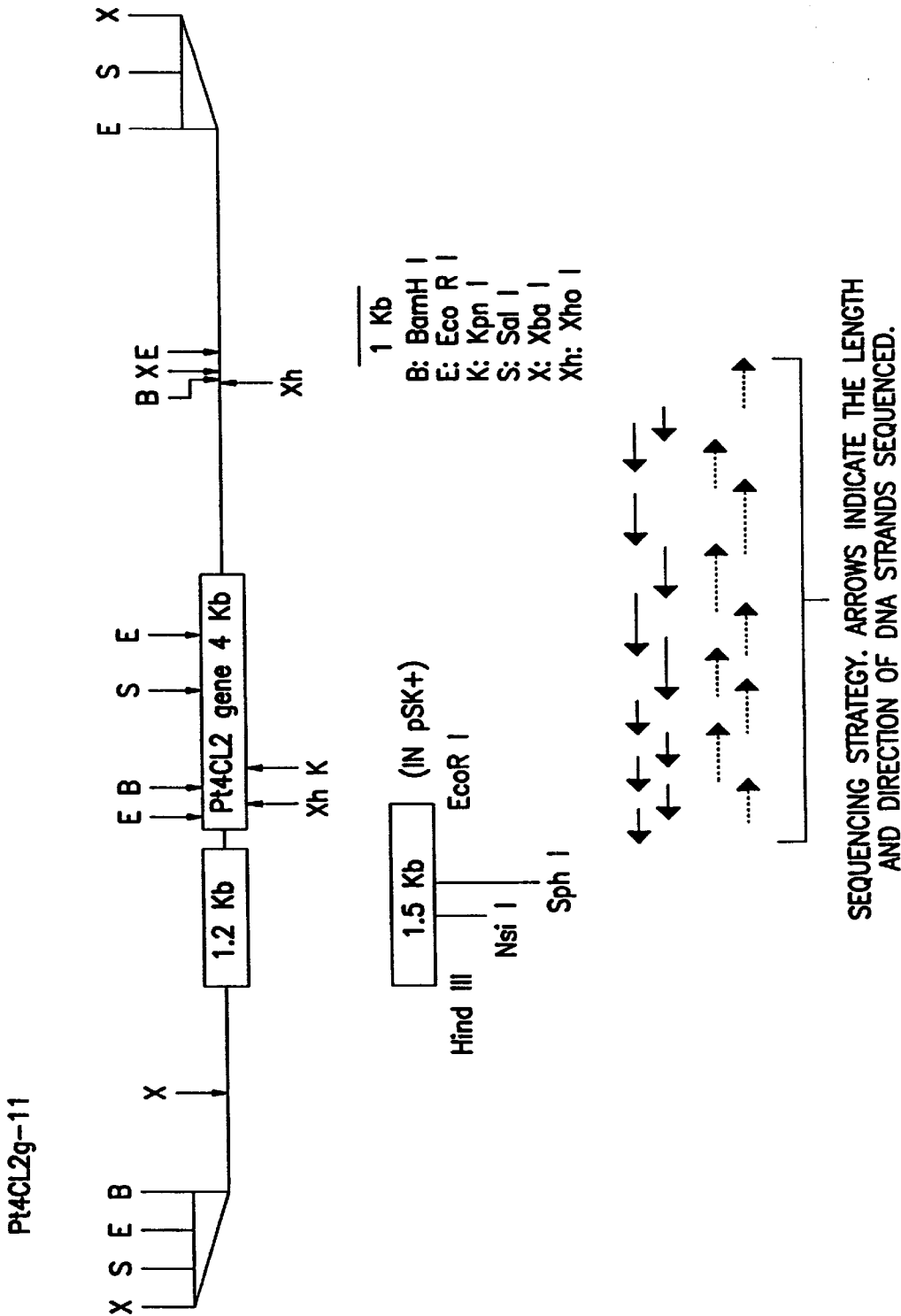
FIG. 4 is a restriction map of genomic clone PtCCL2g-11.

With respect to PtCCL2, restriction map analysis was performed on λDNA of positive genomic clone PtCCL2g-11. The restriction map of PtCCL2g-11 is set forth at FIG. 4.

Figure 5:
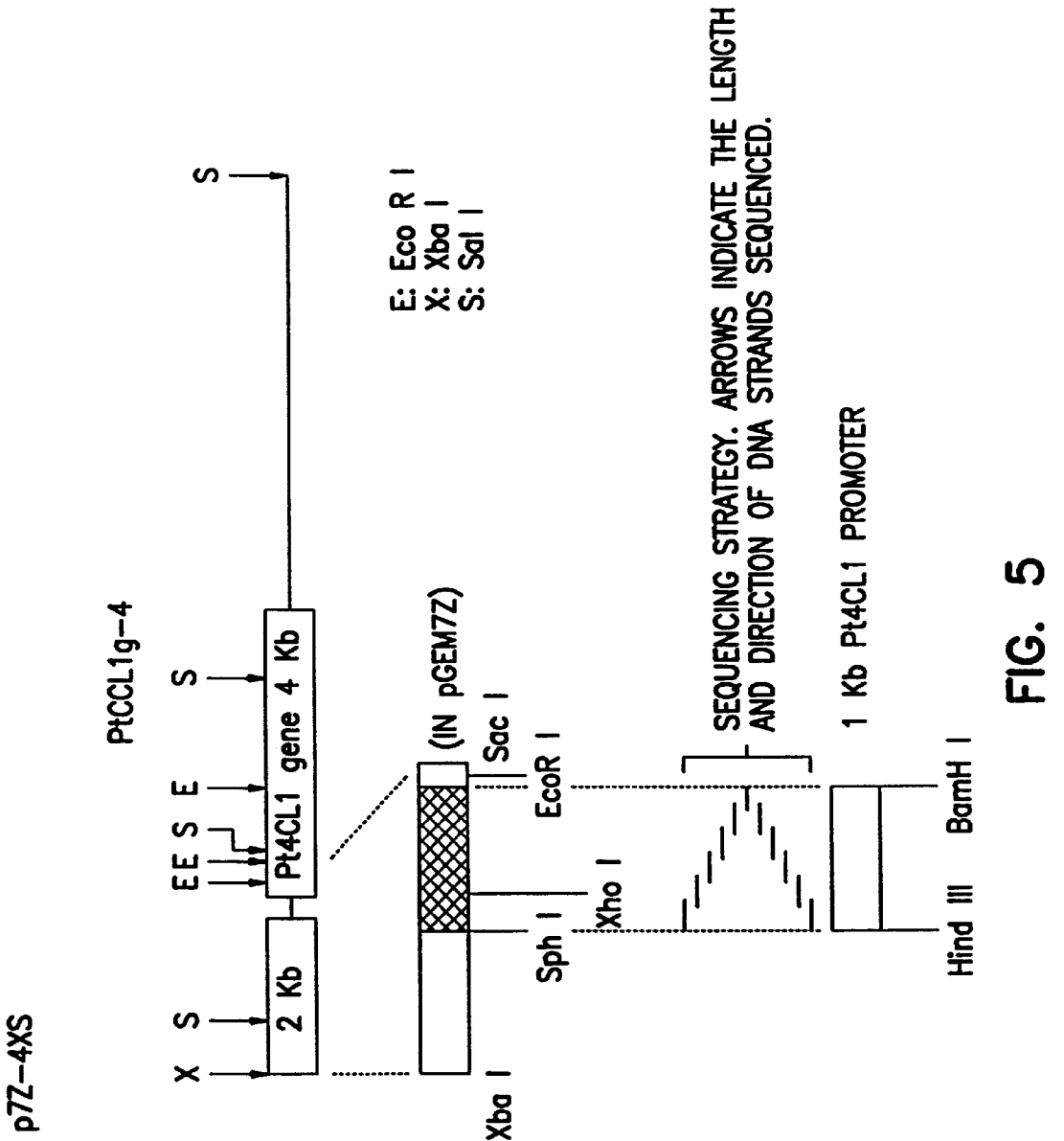
FIG. 5 is a restriction map of subcloned PtCCL1 gene promoter p7Z-4XS.

Approximately a 2.3 kb 5' flanking region of PtCCL1 was digested from PtCCL1g-4 using Xba I and Sac I sites and cloned into pGEM7Z Xba I and Sac I sites. The subcloned PtCCL1 promoter was named p7Z-4XS and the restriction map of P7Z-4XS is set forth at FIG. 5. The 5' unilateral deletion of p7Z-4XS was generated for DNA sequencing by exonuclease III/S1 nuclease digestion using Erase-a-Base System (Promega, Madison, Wis.). The deletion series was sequenced using a primer on pGEM7Z vector.

Figure 6:
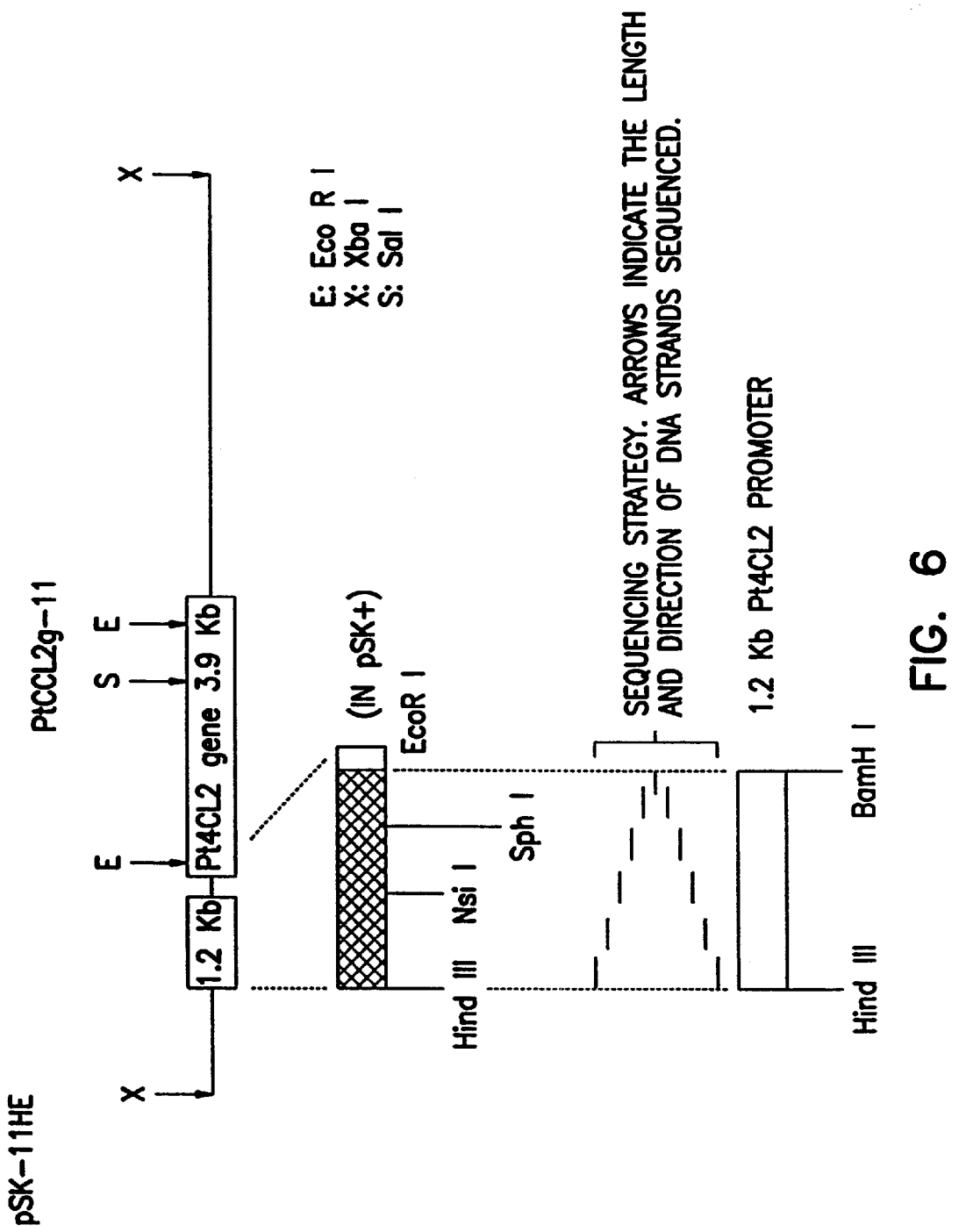
FIG. 6 is a restriction map of subcloned PtCCL2 gene promoter pSK-11HE

A 1.6 kb Hind III and EcoR I fragment containing a 1.2 kb 5' flanking region of PtCCL2 and 0.4 kb coding region of PtCCL2g-11 were subcloned in pBluescript II SK+ Hind III and EcoR I sites. The restriction map of the resulting clone, pSK-11HE, was determined by digesting the plasmid with several restriction enzymes, as in set forth at FIG. 6. In order to determine the sequence of the PtCCL2 promoter, pSK-11HE was further digested into small fragments according to the restriction map and subcloned into vectors with suitable cloning sites. The DNA sequence was determined using M13 universal primer and reverse primer on the vector.

The DNA sequences of the two promoters was determined and analyzed using ΔTaq cycle sequencing Kit (USB, Cleveland, Ohio), and GENETYX-MAC 7.3 sequence analysis software from Software Development Co., Ltd. The nucleotide sequence of promoter region of PtCCL1 is set forth as SEQ ID NO:5 and the nucleotide sequence of the promoter region of PtCCL2 is set forth as SEQ ID NO:6. The promoter gene constructs PtCCL1p and PtCCL2p are available from Michigan Technological University, Institute of Wood Research, Houghton, Mich.

Tissue-specific expression can be achieved by conventionally fusing the promoters of PtCCL1 or PtCCL2 to a gene of interest and transferred to a plant species via Agrobacterium. For the sake of example, the promoters of PtCCL1 and PtCCL2 were fused to a GUS reporter gene as detailed below. However, it should be noted that genes other than the GUS reporter gene can be fused to these promoters for tissue specific expression.

In order to construct PtCCL1 promoter-GUS binary vector, a 1 Kb fragment covering 5'-flanking region and 117 bp coding region of PtCCL1 was subcloned into pGEM7Z Sph I and EcoR I sites for constructing promoter-GUS binary vector. In this 1 kb DNA fragment, it is found that one Xho I site locates at 486 bases proximal to the translation start site and the EcoR I site at 117 bases downstream the translation site. This 0.6 Kb fragment was subcloned into pGEM7Z Xho I and EcoR I sites and used as a template in PCR amplification.

In order to construct a promoter-GUS transcriptional fusion, a BamH I site was introduced in front of the translation start site of PtCCL1 by PCR. PCR amplification was performed using p7Z-4XE as the template, M13 universal primer on pGEM7Z vector as 5' end primer and PtCCL1p-1 primer containing a BamH I site at the end is complementary to a sequence upstream of the translation start site. The reaction was carried out in 100 μl reaction mix containing 1×pfu reaction buffer, 200 μl each dNTPs, 100 μM each primer and 5 units of pfu. The PCR reaction mixture was denatured at 94° C. for 5 minutes followed by 30 cycles of 94° C. (1 minute), 55° C. (1 minute), 72° C. (1 minute, 30 seconds) and was ended with a 5 minute extension at 72° C.

Figure 7:
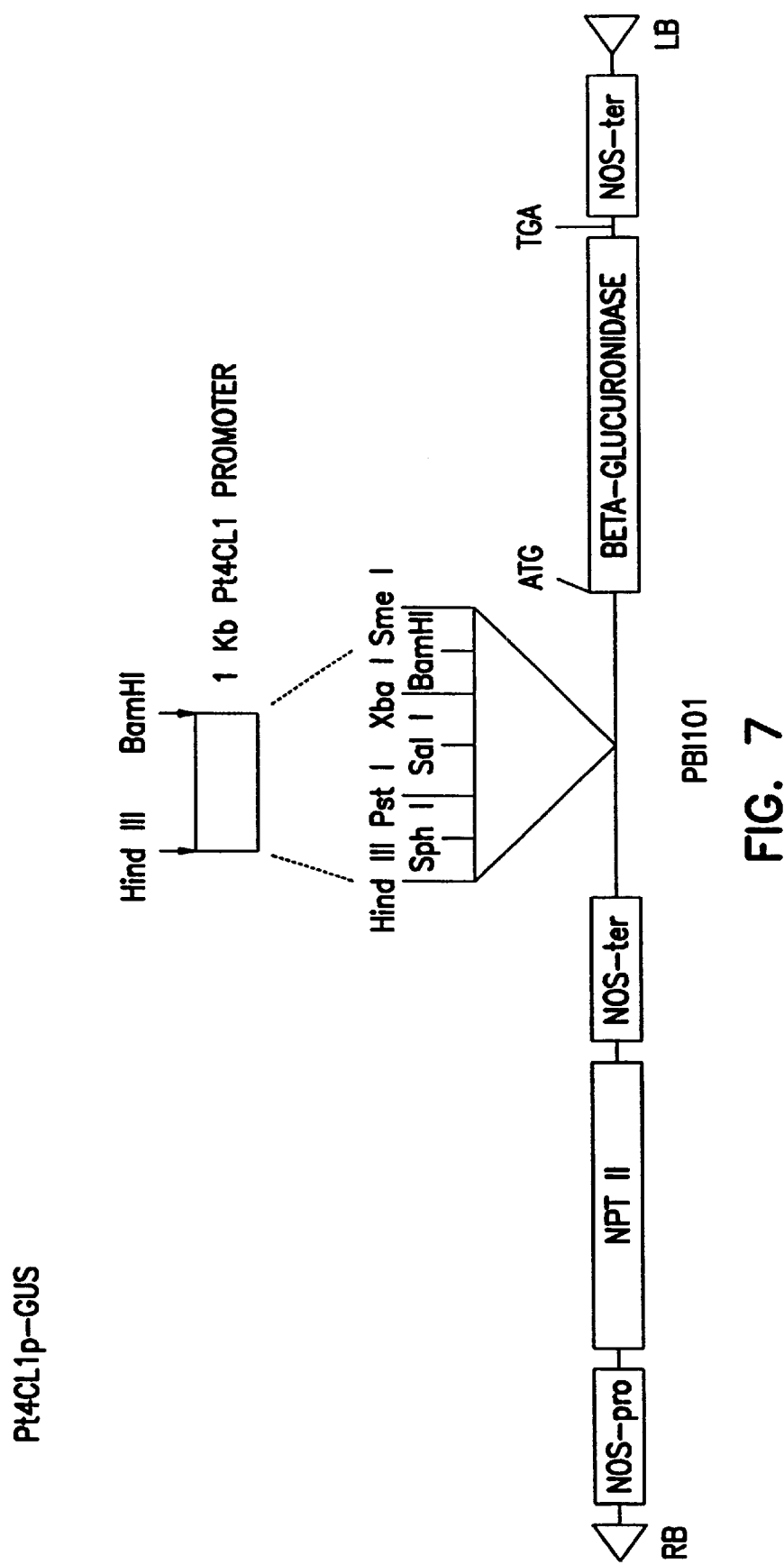
FIG. 7 is an Agrobacterium T-DNA construct of PtCCL1 promoter and GUS fusion gene, PtCCL1p-GUS.

The amplified 0.6 Kb fragment was cloned and sequenced to confirm the sequence. The engineered 0.6 Kb fragment was ligated to p7Z-4SE which was digested with Xho I and BamH I. In order to incorporate a Hind III site in the 5' end of PtCCL1 promoter, the 1 kb Sph I-BamH I PtCCL1promoter region was the cloned into pNoTA (5 prime→3 prime Inc., Boulder, Colo.) Sph I and BamH I site. The 1 Kb PtCCL1promoter was then released from pNoTA vector with Hind III and BamH digestion and subsequently transcriptionally fused to pBI101 Hind III and BamH I sites in front of GUS. The resulting binary vector was named PtCCL1p-GUS and is set forth at FIG. 7.

Figure 8:
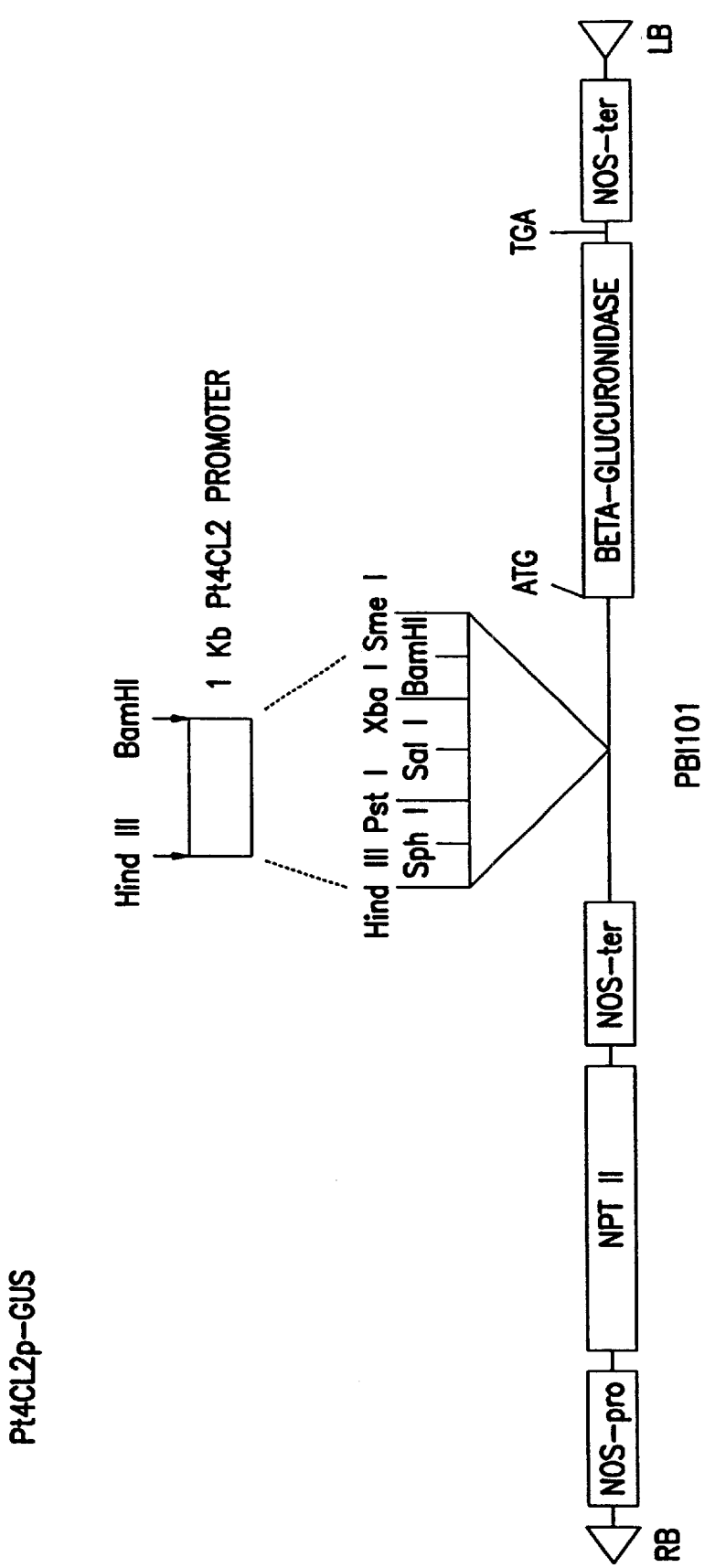
FIG. 8 is an Agrobacterium T-DNA construct of PtCCL2 promoter and GUS fusion gene, PtCCL2p-GUS.

In order to construct PtCCL2 promoter-GUS binary vector, pSK-11HE was digested with Sph I and EcoR I to release 0.2 Kb Sph I and EcoR I fragment. The 0.2 Kb fragment was cloned into pGEM7Z Sph I and EcoR I sites. A primer, PtCCL2p-3' (5'-CATCGGATCCTGAGATGGAAGGGAGTTTCT-3')(SEQ ID NO:14) was designed to be complementary to a sequence upstream of the translation start site of PtCCL2 and to incorporate BamH I site at the end. Amplification was performed using p7Z11SE as a template, M13 universal primer as the 5' end primer and PtCCL2p-3 as the 3' end primer. A PCR reaction was carried out and the amplified PCR product was cloned and sequenced to check the fidelity of the PCR amplification. The 0.2 Kb Sph I-BamH I DNA fragment with correct sequence was fused to pSK-11HE linearized with Sph I and BamH I. The resulting plasmid was named pSK-11HB. The promoter of PtCCL2 was then excised from pSK-11HB with Hind III and BamH I and ligated to PBI101 Hind III and BamH I site to make PtCCL2p-GUS transcriptional fusion binary vector as shown in FIG. 8.

The PtCCL1p-GUS and PtCCL2p-GUS constructs are then mobilized into *Agrobacterium tumefaciens* strain C58/pMP90 by freeze and thaw method as explained previously.

Leaf disk transformation of tobacco with these two Agrobacterium constructs is conducted according to the method of Horsch R. B. (1988) Leaf Disk Transformation, Plant Molecular Biology Manual, A5:1–9. Histochemical GUS staining of promoter-GUS transgenic tobacco plants demonstrated that the PtCCL1 promoter restricted GUS expression in xylem tissue whereas PtCCL2 promoter regulated GUS expression in epidermal cells.

We claim:

1. A method of altering a characteristic of a plant comprising the step of incorporating into the genome of the plant a nucleotide sequence encoding p-coumarate Co-enzyme A ligase (4CL), such that when the nucleotide sequence is expressed in the plant, the characteristic of the plant is altered, wherein the characteristic is selected from the group consisting of altered growth, altered lignin content, increased or decreased coniferyl and sinapyl alcohol units in the lignin structure, increased or decreased disease resistance, altered cellulose content and combinations thereof compared to a control plant that is not transformed with the nucleotide sequence.

2. A plant having a characteristic genetically altered through incorporation into the genome of the plant a nucleotide sequence encoding p-coumarate Co-enzyme A ligase (4CL), such that when the nucleotide sequence is expressed in the plant, the characteristic of the plant is altered, wherein the characteristic is selected from the group consisting of altered growth, altered lignin content, increased or decreased coniferyl and sinapyl alcohol units in the lignin structure, increased or decreased disease resistance, altered cellulose content and combinations thereof compared to a control plant that is not transformed with the nucleotide sequence.

3. The method as set forth in claim 1 wherein the nucleotide sequence is in the anti-sense orientation.

4. The method as set forth in claim 1 wherein the nucleotide sequence is in the sense orientation.

5. The method as set forth in claim 1 wherein the 4CL comprises an AMP-binding region conserved in all 4CL enzymes in the lignin biosynthetic pathway.

6. The method as set forth in claim 1 wherein the nucleotide sequence comprises:

(a) the nucleotide sequence of SEO ID NO:1;

(b) a nucleotide sequence having at least about 60% sequence identity to SEQ ID NO:1; or (c) a nucleotide sequence that is complementary to (a) or (b).

7. The method as set forth in claim 1 wherein the nucleotide sequence has at least 60% identity to the endogenous 4CL gene.

8. The method as set forth in claim 1 wherein the incorporating is by plant transformation.

9. The method as set forth in claim 8 wherein the transformation is Agrobacterium-mediated transformation.

10. The method as set forth in claim 1 wherein the nucleotide sequence is a cDNA.

11. The method as set forth in claim 1 wherein the nucleotide sequence is operably linked to the CaMV 35S promoter.

12. The method as set forth in claim 1 wherein the plant is a tree.

13. The method as set forth in claim 12 wherein the tree is an angiosperm.

14. The method as set forth in claim 12 wherein the tree is a gymnosperm.

15. The method as set forth in claim 1 wherein the altered characteristic is accelerated growth and wherein the accelerated growth is manifested as an increase in the average internode length.

16. The method as set forth in claim 1 wherein the altered characteristic is accelerated growth and wherein the accelerated growth is manifested as an increase in plant height.

17. The method as set forth in claim 1 wherein the altered characteristic is accelerated growth and wherein the accelerated growth is manifested as an increase in plant diameter.

18. The method as set forth in claim 1 wherein the altered characteristic is increased disease resistance and wherein the increased disease resistance is increased fungal pathogen resistance.

19. The method as set forth in claim 1 wherein the nucleotide sequence is contained in a binary vector.

20. The plant as set forth in claim 2 wherein the nucleotide sequence is in the anti-sense orientation.

21. The plant as set forth in claim 2 wherein the nucleotide sequence is in the sense orientation.

22. The plant as set forth in claim 2 wherein the 4CL comprises an AMP-binding region conserved in all 4CL enzymes in the lignin biosynthetic pathway.

23. The plant as set forth in claim 2 wherein the nucleotide sequence comprises:

(a) the nucleotide sequence of SEO ID NO:1;

(b) a nucleotide sequence having at least about 60% sequence identity to SEQ ID NO:1; or (c) a nucleotide sequence that is complementary to (a) or (b).

24. The plant as set forth in claim 2 wherein the nucleotide sequence has at least 60% identity to the endogenous 4CL gene.

25. The plant as set forth in claim 2 wherein the nucleotide sequence is incorporated into the genome of the plant by transformation.

26. The plant as set forth in claim 25 wherein the transformation is Agrobacterium-mediated transformation.

27. The plant as set forth in claim 2 wherein the nucleotide sequence is a cDNA.

28. The plant as set forth in claim 2 wherein the nucleotide sequence is operably linked to the CaMV 35S promoter.

29. The plant as set forth in claim 2 wherein the plant is a tree.

30. The plant as set forth in claim 29 wherein the tree is an angiosperm.

31. The plant as set forth in claim 29 wherein the tree is a gymnosperm.

32. The plant as set forth in claim 2 wherein the altered characteristic is accelerated growth and wherein the accelerated growth is manifested as an increase in the average internode length.

33. The plant as set forth in claim 2 wherein the altered characteristic is accelerated growth and wherein the accelerated growth is manifested as an increase in plant height.

34. The plant as set forth in claim 2 wherein the altered characteristic is accelerated growth and wherein the accelerated growth is manifested as an increase in plant diameter.

35. The plant as set forth in claim 2 wherein the altered characteristic is increased disease resistance and wherein the incrcased disease resistance is increased fungal pathogen resistance.

36. The plant as set forth in claim 2 wherein the nucleotide sequence is contained in a binary vector.

37. The method as set forth in claim 1 wherein the nucleotide sequence encodes a polypeptide comprising the amino acid sequence of SEQ ID NO:2, or a polypeptide comprising an AMP-binding region conserved in all 4CL enzymes in the lignin biosynthetic pathway.

38. The plant as set forth in claim 2 wherein the nucleotide sequence encodes a polypeptide comprising the amino acid sequence of SEQ ID NO:2, or a polypeptide comprising an AMP-binding region conserved in all 4CL enzymes in the lignin biosynthetic pathway.

\* \* \* \* \*